(12) United States Patent
Glover et al.

(10) Patent No.: US 8,633,152 B2
(45) Date of Patent: Jan. 21, 2014

(54) PROCESS FOR MAKING MICRO-SIZED PROTEIN PARTICLES

(75) Inventors: William John Glover, Singapore (SG); Elsa Wan, Singapore (SG); Jimmy Sunglai Yun, Faber Heights (SG); Jianfeng Chen, Beijing (CN)

(73) Assignee: Nanomaterials Technology Pte Ltd, Singapore (SG)

( * ) Notice: Subject to any disclaimer, the term of this patent is extended or adjusted under 35 U.S.C. 154(b) by 402 days.

(21) Appl. No.: 12/672,384

(22) PCT Filed: Jul. 10, 2008

(86) PCT No.: PCT/SG2008/000247
§ 371 (c)(1),
(2), (4) Date: Apr. 27, 2010

(87) PCT Pub. No.: WO2009/020434
PCT Pub. Date: Feb. 12, 2009

(65) Prior Publication Data
US 2011/0129897 A1   Jun. 2, 2011

Related U.S. Application Data

(60) Provisional application No. 60/954,547, filed on Aug. 7, 2007.

(51) Int. Cl.
| | | |
|---|---|---|
| *A61K 38/00* | (2006.01) | |
| *B32B 5/16* | (2006.01) | |
| *B32B 9/00* | (2006.01) | |
| *B32B 15/02* | (2006.01) | |
| *B32B 17/02* | (2006.01) | |
| *B32B 19/00* | (2006.01) | |
| *B32B 21/02* | (2006.01) | |
| *B32B 23/02* | (2006.01) | |
| *B32B 27/02* | (2006.01) | |

(52) U.S. Cl.
USPC .................. 514/1.1; 264/6; 428/402

(58) Field of Classification Search
None
See application file for complete search history.

(56) References Cited

U.S. PATENT DOCUMENTS

| | | | |
|---|---|---|---|
| 6,451,349 B1* | 9/2002 | Robinson et al. | 424/489 |
| 6,838,076 B2* | 1/2005 | Patton et al. | 424/45 |
| 7,138,136 B2* | 11/2006 | Annapragada et al. | 424/450 |
| 2003/0064033 A1* | 4/2003 | Brown et al. | 424/46 |

FOREIGN PATENT DOCUMENTS

| | | | | |
|---|---|---|---|---|
| WO | 2000/00176 A1 | 1/2000 | | |
| WO | 2000/27363 A1 | 5/2000 | | |
| WO | WO 01/93837 | * 12/2001 | | A61K 9/16 |
| WO | WO 2007/053923 | * 5/2007 | | A61K 9/16 |
| WO | WO2007053923 | * 5/2007 | | A61K 9/16 |

OTHER PUBLICATIONS

Chen et al. Feasibility of preparing nanodrugs by high-gravity reactive precipitation. Int J Pharm, 2004, vol. 269, pp. 267-274.*
Chiou et al. Production of salbutamol sulfate for inhalation by high-gravity controlled antisolvent precipitation. Int J Pharm, 2006 (available online Sep. 19, 2006), vol. 331, pp. 93-98.*
Liu et al. Nanoparticle of Conjugated Rifampicin for Aerosol Drug Delivery and Sustained Release. PMSE 167, Paper No. 100402. Presented on Sep. 12, 2006, 232nd ACS National Meeting, San Francisco, CA, Sep. 10-14, 2006.*

* cited by examiner

*Primary Examiner* — Marcela M Cordero Garcia
(74) *Attorney, Agent, or Firm* — Kilpatrick Townsend & Stockon LLP

(57) ABSTRACT

A process of making micro-sized protein particles comprising the step of drying nano-sized protein particles suspended in a liquid medium under conditions to agglomerate the nano-sized protein particles and thereby form micro-sized protein particles.

20 Claims, 15 Drawing Sheets

PROCESS FOR MAKING MICRO-SIZED PROTEIN PARTICLES

TECHNICAL FIELD

The present invention generally relates to a process of making micro-sized protein particles.

BACKGROUND

Modern medicine has relied heavily on synthetically or chemically produced drugs to treat or prevent diseases and conditions in patients. However, in recent times there has been more emphasis on the use of protein-based drugs (also known as "biologics" or biopharmaceuticals"), to prevent and treat diseases and conditions, or to restore or maintain normal body functions of patients. Protein-based drugs are pharmaceuticals based on proteins or portions of proteins such as peptides. Protein-based drugs have become increasingly important in recent years with the advent of high throughput screening and proteomics.

Protein-based drugs do present a difficult challenge for pharmaceutical scientists in that these molecules tend to be large and bulky, making it difficult for them to gain access to target sites of the human body. Protein-based drugs may also be very sensitive to the acid and digestive enzymes of the gut, which makes them unsuitable for oral administration. Accordingly, protein-based drugs, such as insulin, have to be administered parenterally by injection to be efficacious. Patients may need to self-administer several injections each day, which can often result in a lack of compliance by the patient with the use of injections because of the associated inconvenience and pain.

In recent years research has been undertaken to develop alternate delivery systems for the effective delivery of protein-based drugs. One such promising mode of delivery is pulmonary delivery using an aerosol formulation of the protein-based drug. An advantage of pulmonary delivery of drugs to patients is that this mode is rapid because access to the circulation system is via the lungs, which have a large surface area.

Furthermore, administration of drugs through the lungs can bypass the "first pass effect" or "first pass metabolism" commonly associated with drugs absorbed through the gastrointestinal tract (GIT). This "first pass metabolism" refers to metabolism of drugs that occurs between the GIT and the liver before they are available to the systemic circulation system, whereas absorption via the lung allows drugs to directly enter the systemic circulation system without undergoing "first pass metabolism".

Administration of the protein to the lungs is more likely to be accepted by patients and is therefore an attractive alternative to injections, as long as the protein can be formed as fine particles, without significant loss of biological activity. Usual criteria for the use of aerosol delivery for the administration of therapeutic drugs to the lungs are that the drug is in particulate form. To function effectively, the biological activity of the protein must be maintained. However, this can be somewhat difficult to achieve because during synthesis of the protein particles, the biological activity of the protein may be compromised by reducing the particle size of the protein to the low micron range.

A common problem in manufacture of such protein particles is unacceptable variation in particle size. This can be particularly difficult to achieve when the particles need to be in the micro-size range. Furthermore, the process conditions to produce the protein particles within the required size specifications can also be difficult to achieve. Moreover, protein-based drugs are even more challenging to produce because proteins tend to be somewhat fragile molecules and their biological activity needs to be maintained.

Known methods involve spray-drying a solution containing the protein. Spray-drying results in evaporation and hence removal of the solvent due to the high temperatures used. As the solvent evaporates, the concentration of the protein increases beyond the level of saturation. Therefore, the protein precipitates out from the solution to form particles. A problem with this process is that the drying step often results in the formation of particles with relatively large particle size ranges. Hence the particle sizes are not uniform. As mentioned above, the non-uniform particle size compromises the effectiveness of the particles for use in aerosol formulations. Furthermore, the precipitated particles tend to have a non-porous structure which means that they have a higher density as compared to particles with a porous structure, which can again have an adverse impact on suitability of these particles being used in aerosol formulations. Although it is possible to form particles with porous structures, highly specialized and complicated systems as well as excipients are needed. Moreover, spray drying can lead to protein degradation due to physical shear forces experienced by the protein solution as it passes through the nozzles and/or exposure to the high temperatures at which the spray dryer is operated at. In order to retain the biological activity of the protein particles, stabilizing agents are needed. However, these stabilizing agents and the above-mentioned excipients may not be suitable for pulmonary delivery and extra toxicity studies may be needed to determine their suitability and safety.

One known method to manufacture insulin micro-particles involves the atomisation of a solution containing a matrix-forming polymer and insulin, and then directing the resulting droplets into a liquefied gas, typically liquid nitrogen. The droplets freeze on contact with the liquefied gas and may then be dried using a freeze-drying step to remove residual moisture. The resulting micro-sized protein particles comprise the insulin dispersed within the polymer matrix. However a problem with this method is that the biological activity of the particles may be compromised during the freeze drying step. Furthermore, because the formed micro-particles are formed by precipitation during the atomization step, it may be difficult to form particles having a substantially uniform particle size. Moreover, excipients are typically added during this process to enhance the stability of the protein during the freezing step and during storage. A problem with adding excipients is that they may be unsuitable for inhalation delivery. Another problem associated with the above process is that it is not easy for scale-up.

There is a need to provide a process of making micro-sized protein particles that overcomes, or at least ameliorates, one or more of the disadvantages described above. There is also a need to provide micro-sized protein particles that are suitable for use in an inhalation device for pulmonary delivery to a patient.

SUMMARY

According to a first aspect of the invention, there is provided a process of making micro-sized protein particles comprising the step of drying nano-sized protein particles suspended in a liquid medium under conditions to agglomerate the nano-sized protein particles and thereby form micro-sized protein particles.

Advantageously, the micro-sized protein particles have a porous structure. More advantageously, the core of the micro-sized protein particles have a void. More advantageously, the micro-sized protein particles are suitable for pulmonary delivery to a patient.

In one embodiment, there is provided a process of making micro-sized protein particles comprising the steps of:

providing a suspension of nano-sized protein particles having a relatively narrow particle size distribution;

drying said suspension under conditions to agglomerate the nano-sized protein particles and thereby form micro-sized protein particles having a porous inner core.

In one embodiment, there is provided a process of making micro-sized insulin particles comprising the step of drying nano-sized insulin particles suspended in a liquid medium under conditions to agglomerate the nano-sized insulin particles and thereby form micro-sized insulin particles.

In one embodiment, there is provided a process of making micro-sized protein particles comprising the steps of:

applying high shear conditions to a precipitant solution under conditions to form nano-sized protein particles having a relatively narrow particle size distribution;

drying said nano-sized protein particles under conditions to agglomerate the nano-sized protein particles and thereby form micro-sized protein particles having a porous inner core.

According to a second aspect of the invention, there is provided a micro-sized protein particle comprised of a plurality of agglomerated nano-sized protein particles.

More advantageously, the agglomerated nano-sized protein particles have a relatively narrow particle size distribution.

In one embodiment, there is provided a micro-sized protein particle having a substantially porous inner core.

According to a third aspect, there is provided a micro-sized protein particle made in the process of the first aspect.

According to a fourth aspect, there is provided the use of the micro-sized protein particles, as defined in the second aspect, in an inhalation device. In one embodiment, the micro-sized protein particles for use in the inhalation device, is insulin for use by a patient suffering from diabetes.

According to a fifth aspect, there is provided a method of treating a patient with diabetes, or related disease thereof, comprising the step of administering a plurality of micro-sized insulin particles to the lungs of a patient.

Advantageously, in one embodiment, the micro-sized protein particles may be made in the process of the first aspect.

According to sixth aspect, there is provided a medicament for pulmonary delivery to a patient, said medicament comprising a plurality of micro-sized protein particles as defined in the second aspect. In one embodiment, the micro-sized protein particles have a substantially porous inner core. In one embodiment, the micro-sized protein particles may be made in the process of the first aspect.

According to a seventh aspect, there is provided a use of a plurality of micro-sized protein particles as defined in the second aspect, wherein the particles are comprised of insulin, in the manufacture of a medicament for treating diabetes, or related diseases. In one embodiment, the micro-sized insulin particles may be made in the process of the first aspect.

According to an eighth aspect, there is provided a process of making micro-sized protein particles comprising the steps of precipitating a precipitant solution containing protein under high shear conditions in the presence of an anti-solvent to form nano-sized protein particles; and drying the nano-sized protein particles under conditions to agglomerate the nano-sized protein particles and thereby form micro-sized protein particles.

DEFINITIONS

The following words and terms used herein shall have the meaning indicated:

The term "nano-sized" is to be interpreted broadly to relate to an average particle size of less than about 1000 nm, particularly between about 50 nm to about 1000 nm, more particularly less than about 500 nm. The particle size may refer to the diameter of the particles where they are substantially spherical. The particles may be non-spherical and the particle size range may refer to the equivalent diameter of the particles relative to spherical particles.

The term "micro-sized" is to be interpreted broadly to, unless specified, relate to an average particle size of between about 1 µm to about 100 µm. The particle size may refer to the diameter of the particles where they are substantially spherical. The particles may be non-spherical and the particle size range may refer to the equivalent diameter of the particles relative to spherical particles.

The term "precipitant solution" is to be interpreted broadly to refer to any solution which comprises one or more solutes dissolved in a solvent or a mixture of solvents that, when added to an anti-solvent, causes a precipitate to form.

The term "anti-solvent" is to be interpreted broadly to refer to a solvent or a mixture of solvents which, when added in a sufficient quantity to the precipitant solution, cause the solute to precipitate from the precipitant solution without removal or reduction of the solvent medium. The anti-solvent used may be substantially miscible with the solvent of the precipitant solution such that the interaction between the anti-solvent and the solvent allows the solute to precipitate from the precipitant solution. The anti-solvent may comprise salts or compounds that promote precipitation.

The term "liquid medium" is to be interpreted broadly to refer to a mixture of precipitant solution and anti-solvent. The term "liquid medium" is generally used to describe the resultant mixture of precipitant solution and anti-solvent after the precipitating step. The liquid medium does not substantially allow resolubilization of the nano-sized protein particles that are formed during the precipitating step. Accordingly, the nano-sized protein particles are substantially insoluble in the liquid medium. The substantially insoluble nano-sized protein particles are suspended in the liquid medium and this is referred to as a "suspension".

The term "narrow particle size distribution" is to be interpreted broadly to refer to a steepness ratio, as measured on a SEDIGRAPH™ particle size analyzer, of the precipitate particles being less than about 3. The size distribution of the precipitate particles in a given composition may be represented on a SEDIGRAPH™ which plots cumulative mass percent as a function of particle size, where cumulative mass percent is the percent, by weight, of a distribution having a particle size of less than or equal to a given value and where particle size is the diameter of an equivalent spherical particle. The mean particle size in a distribution is the size in micrometers or nanometers of the precipitate particles at the 50% point on the SEDIGRAPH™ for that distribution. The width of the particle size distribution of a given composition can be characterized using a steepness ratio. As used herein, the "steepness ratio" is defined as the average diameter of the particles in the seventy-fifth mass percentile divided by the average diameter of the particles in the twenty-fifth mass percentile. The "narrow particle size distribution" may also refer to a span value of the precipitate particles as being less than about 2. The span value is defined as Span=([particle diameter at 90% cumulative size]-[particle diameter at 10% cumulative size])/[particle diameter at 50% cumulative size].

The term "high shear" is to be interpreted broadly to refer to a condition when the shear force applied within a mixing zone may have a Reynolds number in the range selected from the group consisting of 2000-200000, 5000-150000, 8000-100000. The high shear created may enable a high degree of mixing in the mixing zone.

The term "agglomeration" and related term "agglomerated" is to be interpreted broadly to refer to an assemblage of a plurality of nano-sized protein particles which are either loosely or rigidly joined together as a consequence of a drying step.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DETAILED DISCLOSURE OF EMBODIMENTS

Exemplary, non-limiting embodiments of a process of making micro-sized protein particles will now be disclosed.

The process comprises the step of drying nano-sized protein particles suspended in a liquid medium under conditions to agglomerate the nano-sized protein particles and thereby form micro-sized protein particles.

The micro-sized protein particles obtained may have a particle size that is in the range selected from the group consisting of about 1 μm to about 10 μm; about 1 μm to about 9 μm; about 1 μm to about 8 μm; about 1 μm to about 7 μm; about 1 μm to about 6 μm; about 1 μm to about 5 μm; about 1 μm to about 4 μm; about 1 μm to about 3 μm; about 1 μm to about 2 μm; about 2 μm to about 10 μm; about 3 μm to about 10 μm; about 4 μm to about 10 μm; about 5 μm to about 10 μm; about 6 μm to about 10 μm; about 7 μm to about 10 μm; about 8 μm to about 10 μm; about 9 μm to about 10 μm. In embodiments where the micro-sized protein particle is substantially spherical in shape, the above particle size refers to, for particles that are not completely spherical, the equivalent diameter of the micro-sized protein particle, wherein said equivalent diameter is relative to a completely spherical diameter. In some embodiments, the micro-sized protein particles are completely spherical and the equivalent diameter is equal to the actual diameter of the micro-sized protein particles.

The micro-sized protein particles may have a porous structure. The micro-sized protein particles may have an inner core which is a void. The porosity or amount of void space in the micro-sized protein particles may be in the range selected from the group consisting of about 10% to about 80%; about 10% to about 70%; about 10% to about 60%; about 10% to about 50%; about 10% to about 40%; about 10% to about 30%; about 10% to about 20%; about 20% to about 80%; about 30% to about 80%; about 40% to about 80%; about 50% to about 80%; about 60% to about 80%; about 70% to about 80%; and about 50% to about 60%.

The tap density of the micro-sized protein particles may be in the range of about 0.1 g/cm$^3$ to about 1 g/cm$^3$. In one embodiment, the tap density of the micro-sized protein particles may be less than about 0.3 g/cm$^3$. In one embodiment, the tap density of the micro-sized protein particles may be less than about 0.2 g/cm$^3$. Tap density is a standard measure of the envelope mass density of the micro-sized protein particles. When the micro-sized protein particles have a substantially spherical shape, the envelope mass density is defined as the mass of the particle divided by the minimum sphere envelope volume within which it can be enclosed.

The mass median aerodynamic diameter of the micro-sized protein particles may be in the range between about 0.5 μm and about 5 μm. In one embodiment, the mass median aerodynamic diameter is between about 1 μm and about 3 μm. In another embodiment, the mass median aerodynamic diameter is between about 3 μm and about 5 μm. In another embodiment, the mass median aerodynamic diameter is between about 2 μm and about 3 μm. In yet another embodiment, the mass median aerodynamic diameter is about 2.31 μm.

The micro-sized protein particles may be in a form suitable for use in a pulmonary delivery device such as an metered-dose inhaler, a dry powder inhaler, or a nebulizer. The micro-sized protein particles may be delivered to the lungs of a patient during use of the pulmonary delivery device. A more detailed discussion on the types of pulmonary delivery devices and their characteristics can be found in the article titled *Inhalation Devices and Propellants* from Canadian Medical Association Journal, 30 Nov. 1999; 161 (90111), the disclosure of which is incorporated herein in its entirety. In the context of dry powder inhalers, the micro-sized protein particles may be formulated in compositions further comprising bulk carrier particles, which aid delivery. Suitable carrier particles are known, and include crystalline lactose particles, with an equivalent diameter typically in the range of from 30 μm to 300 μm, more usually from 50 μm to 250 μm. Depending on the dosage amount to be delivered to the lungs, the type of delivery device used and the dispersion properties of the protein particles once it leaves the delivery device, carrier particles may or may not be needed.

The protein may be selected from the group consisting of insulin, albumins, parathyroid hormones, gonadotropin-releasing hormones, DNAse, cyclosporins, immunoglobulins, erythroprotein, interferons, colony stimulating factors, growth hormones such as Growth Hormones Releasing Hormones (GHRH), luteinising-hormone releasing hormone (LHRH) analogs, LHRH antagonists, tissue plasminogen activator, somatostatin analog, Factor VIII, r Factor IX, calcitonin, abciximab, dornase alfa, polysaccharides, AG337, bone inducing protein, bone morphogenic protein, brain derived growth factor, gastrin 17 immunogen, interleukins, polymerase enhancing factor superoxide, chimeric monoclonal antibody, permeability increasing protein-21, platelet derived growth factor, stem cell factor, Thyrogen®, somatomedin C and mixtures thereof.

In one embodiment, the protein is insulin. The insulin can be selected from the group consisting of a naturally occurring insulin, a semisynthetic insulin, a synthetic insulin, a recombinant insulin, a long-acting insulin, a short-acting insulin and mixtures thereof. The insulin may be selected from the group consisting of lisproinsulin, humalog insulin, porcine insulin, bovine insulin, hepatoselective insulin, or a mixture of any of the foregoing insulins or analogs thereof. Exemplary insulin analogs include, without limitation, "Lyspro" (commercially available from Eli Lilly Co.), LysB28 insulin, ProB29 insulin and AspB28 insulin.

The micro-sized insulin particles obtained may be used to treat a number of diseases that are related to insulin. Two broad categories of diseases that may be treated by administration of insulin to a patient in need thereof include hyperglycemia (excess amount of glucose in the blood plasma) and insulin resistance (when normal amount of insulin are inadequate to produce a normal insulin response).

Diseases where hyperglycemia is a symptom include diabetes mellitus type I or insulin dependent diabetes mellitus (IDDM) which is characterized by loss of insulin producing beta cells in the pancreas; diabetes mellitus type II or non-insulin dependent diabetes mellitus (NIDDM) which is due to defective insulin secretion; gestational diabetes which resembles NIDDM and involves inadequate insulin secretion and response of the mother during gestational period; disease of the pancreas; hormone defects; and drugs.

Diseases where insulin resistance is present include metabolic syndrome and polycystic ovarian syndrome.

Insulin can be administered to a patient via syringes (subcutaneous administration), pumps and jet injectors (through the skin).

For subcutaneous administration, there are many different modes of administration including rapid acting (duration of 5 minutes to 4 hours), short acting (duration of 30 minutes to 8 hours), intermediate acting (duration of 1 hour to 24 hours), long acting (duration of 4 hour to 28 hours) and mixtures thereof. Pumps can be used to administer insulin continuously or in pulses.

The micro-sized protein particles may be formed during the step of drying nano-sized protein particles. The drying step may be spray-freeze drying or spray drying.

During the drying step, more than one type of nano-sized protein particles suspended in the liquid medium may be mixed together and dried. This may result in the formation of micro-sized protein particles that are made up of more than one class of protein. For example, a first suspension of short-acting insulin nano-sized particles may be dried with a second suspension of a long-acting analogue of insulin nano-sized particles to form micro-sized insulin short- and long-acting particles. This may aid in the treatment of diseases where a combination of proteins are desired as the therapeutic agent. Furthermore, this may aid in increasing patient compliance during the treatment if a combination of proteins is administered in a singular inhalation dose to the patient.

Furthermore, in another embodiment, one of the proteins may be inert while the other is biologically active to a target site. For example, a first suspension of nano-sized insulin particles may be dried with a second suspension of inert proteins to form a mixture of protein particles in which the biologically active protein (ie the insulin) is mixed with the inert protein. This allows the dosage regime to be adjusted and carriers are not needed. Hence, the micro-sized protein particles may further comprise inert protein that does not bind to a target site.

In one embodiment, the drying step is undertaken without the use of a binder to agglomerate the nano-sized protein particles. The protein may be biologically active to a target. Advantageously, the drying step may not substantially degrade the biologically activity of the protein. The process may further comprise a protein that is not biologically active to a target.

In one embodiment, the drying step is spray-drying. Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solution in which the nano-sized particles are suspended. Typically the nano-particles, while suspended in the liquid medium, are atomized by an atomizer to form an atomized droplet wherein the liquid of the atomized droplet is rapidly evaporated by application of heat. Due to the small nature of the atomized droplet, and the application of heat, the liquid medium is rapidly evaporated.

The inventors have surprisingly discovered that by rapidly spray drying the suspension, the nano-sized protein particles are drawn together and agglomerate. Without being bound by theory, it is thought that when a plurality of the nano-sized protein particles are spray dried, they are caused to agglomerate within the atomized droplets due to the surface tension exerted on the nano-sized protein particles at the liquid/gas interface of the shrinking (evaporating) droplets. Furthermore, it is thought that, if the nano-sized protein particles are selected to have a relatively small particle size distribution, they are forced together at the same rate until hindrance created by the packing of the nano-sized protein particles prevents further shrinking. Depending on the size of the nano-sized protein particles and the evaporation rate, this can leave a void in the centre of the micro-sized protein particle upon formation by the agglomerated nano-sized protein particles. As the nano-sized protein particles agglomerate, a minute amount of liquid medium may be trapped in the center of the micro-sized protein particle that is being formed. Due to the differences in the temperature and volume of the drying gas as compared to those of the micro-sized protein particles, heat transfer from the drying gas to the micro-sized protein particles is almost instantaneous such that it causes the liquid medium in the center of the micro-sized protein particles to vaporize and thereby form the void.

In one embodiment, a spray dryer using rotary atomization such as the MOBILE MINOR™ spray drier by Niro A/S of Soborg, Denmark is used. In another embodiment, a spray dryer using nozzle atomizers such as the BUCHI™ 290 laboratory scale spray dryer from BUCHI Labortechnik AG of Switzerland is used.

The physical properties of the spray-dried micro-sized protein particles depend on a number of parameters such as direction of flow of the drying gas in the drying chamber; the degree and uniformity of atomization due to the type of atomizer used; the amount of nano-sized protein particles in the liquid medium in % solids concentration; the temperature of the liquid medium; efficiency of the collection mechanism and choice of anti-solvent used.

The flow of the drying gas in the drying chamber may be substantially opposite to the flow of the atomized solution (that is, countercurrent flow) or the flow of the drying gas in the drying chamber may be in the same direction as the flow of the atomized solution (that is, cocurrent flow). Some spray dryers may combine both countercurrent and cocurrent flow in the drying chamber. The type of flow pattern in the drying chamber may aid in the generation of turbulence in the drying chamber and hence, may lead to an increased rate of interaction between the drying gas and the atomized droplets in order to increase the rate of heat transfer from the drying gas to the atomized droplets.

Atomization of the suspension into droplets may be effected through atomizing devices such as rotary atomizers and nozzle atomizers. Exemplary nozzle atomizers include pressure nozzles and two-fluid nozzles. The types of atomizers used may determine the size of the atomized droplets, the degree of atomization as well as the spray characteristics such as spray angle or spray direction of the droplets sprayed from the atomizers into the drying chamber.

The amount of suspended nano-sized protein particles (in % solids concentration) present in the liquid medium may be in a range selected from the group consisting of about 0.1% to about 10%; about 0.1% to about 1%; about 0.1% to about 0.9%; about 0.1% to about 0.8%; about 0.1% to about 0.7%; about 0.1% to about 0.6%; about 0.1% to about 0.5%; about 0.1% to about 0.4%; about 0.1% to about 0.3% and about 0.1% to about 0.2%.

The temperature of the suspension prior to spray drying may be in the range of 4° C. to about 40° C. Without being bound by theory, it is thought that if the temperature of the suspension is within this range, it may aid in the agglomeration of the nano-sized protein particles to form the micro-sized protein particles during spray-drying. It is to be appreciated that the choice of temperature for the suspension should not cause any substantial degradation of the nano-sized protein particles suspended in the liquid medium. In one embodiment, the temperature of the suspension prior to spray drying may be about 20° C.

The inlet temperature of the drying gas into the spray dryer may be in a range selected from the group consisting of about 50° C. to about 150° C.; about 50° C. to about 70° C.; about 50° C. to about 90° C.; about 50° C. to about 110° C.; about 50° C. to about 130° C.; about 70° C. to about 150° C.; about 90° C. to about 150° C.; about 110° C. to about 150° C. and about 130° C. to about 150° C. The outlet temperature may be dependent on the inlet temperature selected and is typically in the range of about 20° C. to about 90° C. In one embodiment, the outlet temperature may be kept below 50° C. in order to ensure that the biological activity of the protein is retained.

The drying time to convert a droplet to dry powder may be less than about 10 seconds, particularly less than about 5 seconds and more particularly about 1 second.

The process may comprise the step of providing the nano-sized protein particles with a relatively narrow particle size distribution. The dimension of the nano-sized protein particles may be in a range selected from the group consisting of about 50 nm to about 1000 nm; about 50 nm to about 500 nm; about 50 nm to about 100 nm; about 50 nm to about 200 nm; about 50 nm to about 300 nm; about 50 nm to about 400 nm; about 100 nm to about 500 nm; about 200 nm to about 500 nm; about 300 nm to about 500 nm and about 400 nm to about 500 nm. In embodiments where the nano-sized protein particle is substantially spherical in shape, the above particle size refers to, for particles that are not completely spherical, the equivalent diameter of the nano-sized protein particle, wherein said equivalent diameter is relative to a completely spherical diameter. In some embodiments, the nano-sized protein particles are completely spherical and the equivalent diameter is equal to the actual diameter of the nano-sized protein particles.

In order to obtain nano-sized protein particles for the above drying step, the process may comprise the step of precipitating nano-sized protein particles from a precipitant solution. The precipitant solution may comprise the desired protein (solute) dissolved in a suitable solvent. The solvent is chosen such that it is capable of dissolving the protein. It is to be appreciated that a person skilled in the art would know what solvent to use in order to dissolve a desired protein. For example, the solvent used may be selected from the group consisting of water, buffered solution, dimethyl sulfoxide, ethanol, methanol, acetonitrile, N-methylpyrrolidone and acidic solutions. A mixture of the above solvents may be used to dissolve the protein.

As the solubility of most proteins in the above solvent is substantially similar to each other, a mixture of two or more classes of proteins may be substantially dissolved in the solvent. As the proteins precipitate out from the precipitant solution during the precipitating step, individual nano-sized protein particles may be formed that are made up of two or more classes of proteins. When these nano-sized protein particles are subsequently dried, micro-sized protein particles may be formed that are made up of two or more classes of proteins. As discussed above, this is advantageous in situations where treatment of diseases require a combination of protein as the therapeutic agent and this may aid in increasing patient compliance.

The precipitating step may be conducted in a micro-mixing environment. In the micro-mixing environment, a shear force may be applied to the precipitant solution in the presence of an anti-solvent in order to form nano-sized protein particles in the mixing zone of the micro-mixing unit.

The anti-solvent may be chosen such that it allows the protein to precipitate from the precipitant solution and form nano-sized protein particles. The anti-solvent may be an alcohol with one to five carbon atoms. The alcohol may be selected from the group consisting of methanol, ethanol, n-propanol, isopropanol, n-butanol, sec-butanol, isobutanol, tert-butanol, n-pentanol, 3-methly-1-butanol, 2-methly-1-butanol, 2,2-dimethyl-1-propanol, 3-pentanol, 2-pentanol, 3-methyl-2-butanol and 2 methyl-2-butanol as well as derivatives thereof. The anti-solvent may be a ketone with three to five carbon atoms. The ketone may be selected from the group consisting of propanone, butanone, 2-propanone and 3-propanone, as well as their derivatives and isomeric forms thereof. In other embodiments, the anti-solvent may be selected from the group consisting of halogenated alkane solutions such as dichloromethane, chloroform, alkane solutions such as hexane, cyclohexane, ether solutions such as diethyl ether, isopropyl ether, and carboxylic acid solutions such as ethyl acetate, and mixtures thereof.

It is to be appreciated that as the anti-solvent is to be substantially miscible with the solvent, the type of anti-solvent chosen will be dependent on the type of solvent used. Therefore, a person skilled in the art understands that this includes all miscible solvents/anti-solvent systems.

Furthermore, the type of solvent or anti-solvent chosen should be selected such that it does not substantially affect the biological activity, chemical properties or the physical integrity of the protein.

Salts may be added to the precipitant solution or anti-solvent as precipitation aids to initiate precipitation of the nano-sized protein particles or to enhance the precipitation rate of the nano-sized protein particles. Exemplary salts useful as precipitation aids may include ammonium salts, such as ammonium acetate, ammonium hydrogen carbonate, ammonium chloride or ammonium sulphate or mineral salts such as sodium chloride, calcium chloride or sodium sulphate. The use of precipitation aids may enable a wide variety of solvent systems (such as water solvent/organic anti-solvent systems with varying volumetric ratio or salt concentrations) to be used.

Advantageously, the shear force applied in the mixing zone forms the nano-sized protein particles having a relatively narrow particle size distribution characterized in that the steepness ratio or span value of the final nano-sized protein particles suspended in the liquid medium is less than about 3, or less than about 2, or less than about 1.9, or less than about 1.8, or less than about 1.7, or less than about 1.6, or less than about 1.5, or less than 1.3.

The process may comprise the step of agitating the mixture of precipitant solution and anti-solvent substantially throughout the mixing zone to induce the shear force. The shear force within the mixing zone may have a Reynolds number in the range selected from the group consisting of 2000-200000, 5000-150000, 8000-100000, thereby enabling a high degree of mixing in the mixing zone.

In one embodiment, the mixing zone is located within an enclosed chamber of a molecular mixing unit. The molecular mixing unit may comprise an agitator within the enclosed chamber. The molecular mixing unit may further comprise at least two fluid inlets to introduce fluids such as the precipitant solution and the anti-solvent into the enclosed chamber and optionally one outlet to allow suspended nano-sized protein particles to be removed from the enclosed chamber.

The use of an agitator to impart high shear to the mixing zone ensures that the precipitant solution and the anti-solvent are adequately and homogeneously mixed in very short time (i.e. less than 10 s, preferably less than 1 s, more preferably less than 10 ms) to form an intimate mixture leading to formation of a precipitate of nano-sized protein particles.

In order to meet the requirement of micro-mixing for precipitation in a very short time, the molecular mixing unit may be operated under a turbulent state in order to impart high shear to the mixing zone and to mechanically mix the precipitant solution and the anti-solvent. The precipitant solution and the anti-solvent in the molecular mixing unit are quickly mixed by the turbulent fluid flow. Therefore, the Reynolds Number shall be regulated on the basis of the equation of:

$$Re = \frac{d \cdot u \cdot \rho}{\mu}$$

wherein, d is the diameter of the pipe (or distributor in the molecular mixing unit) providing the liquid stream (ie precipitant solution or anti-solvent) to the molecular mixing unit, u is the flow speed of the liquid stream, ρ is the density of the liquid stream and μ is the viscosity of the liquid stream.

The relationship of the diameter of the pipe or distributor, the flow speed and flux is shown in the equation of:

$$Q = \frac{\pi \cdot d^2 \cdot u}{4}$$

wherein, Q is the flux of the liquid stream. As can be seen, once the diameter of the pipe or distributor is determined, the flow speed is determined by the flux of the liquid stream. It shall be further noted that a pressure is required to maintain the flux of the ejected flow. Therefore, the related parameters can be concluded as the diameter of pipe, the flux, the pressure and the Reynolds Number.

In one embodiment, the agitator comprises a rotator-stator (or rotor-stator) disposed within an enclosed chamber, the rotator (or rotor) being rotatable about a longitudinal axis for imparting a high shear force to the mixture of precipitant solution and anti-solvent within the mixing zone.

In one embodiment, the agitator comprises a packed bed disposed within the enclosed chamber, the packed bed being rotatable about a longitudinal axis for imparting a shear force to the mixture of precipitant solution and anti-solvent within the mixing zone in use. The packing may have a surface area in the range of about 100-3000 $m^2/m^3$. The packing can be such that it is structured packing or random packing. In one embodiment, the packing is a packing of the wire mesh type packing that can be made from a relatively inert material such as stainless steel, plain metal alloy, titanium metal or plastic.

In one embodiment the packing is substantially cylindrically-shaped and comprises at least one mesh layer. In one embodiment the packing is comprised of a plurality of overlapping mesh layers.

Applying a shear force to the mixture of precipitant solution and anti-solvent within the mixing zone may be undertaken by a shear means. In one embodiment, the shear means is in the form of a rolling mesh to form a cylindrical shear means, wherein the cylindrical section has sides formed by a plurality of overlapping mesh layers. The mesh may have a mesh size of about 0.05 mm to about 3 mm or about 0.1 mm to abut 0.5 mm. The mesh may have mesh porosity of at least 90%, or more than 95%.

In one embodiment, the packed bed is mounted on a shaft in the mixing zone and rotates in the mixing zone. As the packed bed rotates, the packing imparts high shear onto the injected precipitant solution and anti-solvent. In one embodiment, the rotating packed bed is cylindrically shaped and defines a hollow to accommodate the inlets for the precipitant solution and anti-solvent.

Advantageously, in order to meet the requirement of micro-mixing of the precipitant solution and anti-solvent within a very short period of time, the agitator rotates in the mixing zone at a speed to achieve a high-gravity level $g_r$ ($m/s^2$) sufficient to input high shear to the mixture of precipitant solution and anti-solvent in the mixing zone. The high-gravity level can be regulated based on the equation of:

$$g_r = (2\pi N/60)^2 \cdot \frac{d_{in} + d_{out}}{2}$$

where N is the rotating speed of the agitator in rpm, $d_{in}$ is the inner diameter and $d_{out}$ is the outer diameter of the agitator.

The high gravity level is selected from the group consisting of about 100 to about 15000 $m \cdot s^{-2}$, about 500 to about 2000 $m \cdot s^{-2}$, about 1000 to about 5000 $m \cdot s^2$, and about 800 to about 5000 $m \cdot s^{-2}$. The use of such a strong high-gravity level of the agitator ensures that the precipitant solution and anti-solvent in the mixing zone are subjected to strong shear immediately upon injection into the mixing zone.

In one embodiment, the precipitant solution and anti-solvent are injected into the mixing zone via a plurality of the inlets extending through a mixing chamber surrounding the mixing zone. The inlets may be arranged in a number of ways depending on the structural design of the mixer. In one embodiment, the inlets are located in a distributor capable of distributing the precipitant solution and anti-solvent into the mixing zone. The distributor may comprise a body having a plurality of inlets for each of the precipitant solution and anti-solvent.

In one embodiment, the precipitant solution and anti-solvent are respectively injected into the mixing zone via separate inlets.

The mixing unit may comprise at least one liquid outlet means for draining the suspension of nano-sized protein particles in the liquid medium from the mixing zone when the mixing unit is operated in either batch mode or continuous mode.

The drained suspension can be fed directly into the inlet of the drying unit. This allows for the possibility of an integrated unit made up of the micro-mixing unit and the drying unit. This may allow for the possibility of scaling up to larger capacities and hence increases the yield of micro-sized protein particles obtained.

The process may comprise the step of pre-treating the suspension before the drying step. The pre-treating step may result in the removal of salts that may be present in the precipitant solution or the anti-solvent making up the liquid medium. This may aid in increasing the rate of agglomeration of the nano-sized protein particles to form micro-sized protein particles. The pre-treating step may comprise washing the suspension prior to the drying step. The pre-treating step may comprise filtering the nano-sized protein particles from a liquid medium.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DESCRIPTION OF DRAWINGS

Figure 1:
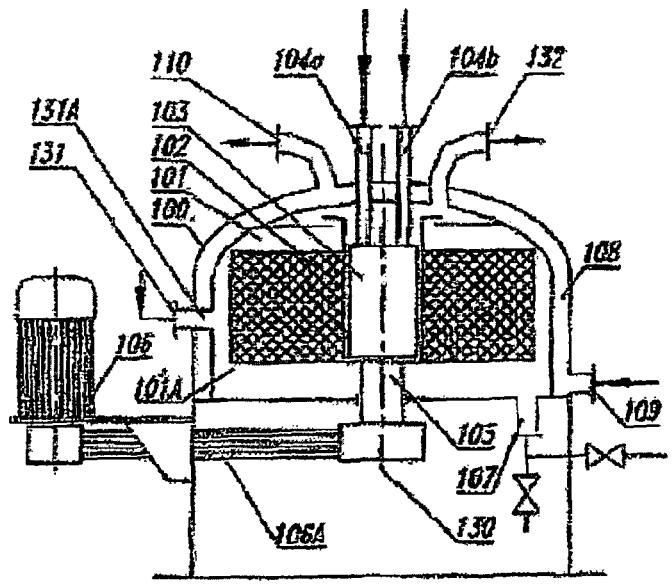
FIG. 1 shows a schematic drawing of a molecular mixing unit for making the nano-sized protein particles according to one disclosed embodiment.

Referring to FIG. 1, there is shown a molecular mixing unit 100. The molecular mixing unit 100 comprises a chamber 101 encompassing an enclosed space which defines a mixing zone 101A in which mixing of the precipitant solution and the anti-solvent occurs in order to result in precipitation of nano-sized protein particles.

The chamber 101 also comprises an agitator in the form of a packed bed 102. The packed bed 102 imparts high shear to the mixture of precipitant solution and anti-solvent within the mixing zone 101A. The packed bed 102 comprises a distributor 103 having two liquid inlets 104a and 104b for respectively feeding the precipitant solution and the anti-solvent into the mixing zone 101A.

The packed bed 102 is mounted on a rotatable shaft 105 disposed on a longitudinal axis represented by line 130. The packed bed 102 is mounted adjacent to the length of the distributor 103. The packed bed 102 is driven by a motor 106 via gear and pulley system 106A. In use, the motor 106 rotates the shaft 105 about the longitudinal axis 130.

The packed bed 102 is in fluid communication with the distributor 103. The distributor 103 comprises a body having conduits for transmission of precipitant solution or anti-solvent onto the packed bed 102. The distributor 103 is in fluid communication with inlet conduits 104a and 104b, which are respectively used for introducing precipitant solution and anti-solvent into the molecular mixing unit 100.

The molecular mixing unit 100 also comprises an outlet conduit 107 for allowing the formed precipitate nano-sized protein particles to be removed from the chamber 101. The material of the molecular mixing unit 100 is stainless steel of 316 grade.

The packed bed 102 is substantially cylindrical in shape and comprises a structured arrangement of a plurality of layers of wire mesh having a mesh size of 0.05 mm. The wire mesh is also made from stainless steel of 316 grade.

A temperature jacket 108 surrounds the chamber 101 to regulate the temperature within the mixing zone 101A. The temperature jacket 108 comprises a jacket inlet 109 for allowing heated fluid to enter and a jacket outlet 110 for allowing the fluid to exit from the jacket 108.

The outer shell of the molecular mixing unit shown in FIG. 1 includes a gas zone 131A above the mixing zone 101A, which may consist of an inert gas such as nitrogen, air or enriched oxygen. The gas zone 131A is created by pumping gas into the chamber 101 via gas-inlet 131 and gas is removed via gas-outlet 132.

The gas zone 131A consists of nitrogen when it is desired to isolate the mixing zone 101A from oxygen. The gas zone 131A consists of either air or enriched oxygen when it is desired that the mixing zone 101A be exposed to oxygen, thereby intensifying gas-liquid mass transfer. Hence, the gas zone 131A is able to function as a barrier for isolating the mixing zone 101A from oxygen and as a gas purge to contact air or oxygen with the mixture of precipitant solution and anti-solvent. Whilst the gas zone 131A is shown in FIG. 1, in other embodiments, it may not be desirable to have the gas zone for certain compounds. Different particle morphologies can be achieved by injecting or purging different gases into the mixing zone.

The distributor 103 ejects the precipitant solution and the anti-solvent from the liquid feed inlets 104a and 104b respectively into the inner surface of the packed bed 102. The precipitant solution and the anti-solvent are mixed together to form a mixture in the packed bed 102 and the chamber 101. The mixture of precipitant solution and anti-solvent passes through the packed bed 102 in a radial direction toward the outer surface of the packed bed 102.

In the packed bed 102, the mixture of Precipitant solution and anti-solvent is subjected to high shear forces in the form of centrifugal forces created by the rotational motion of the shaft 105 and the packed bed 102 about the longitudinal axis 130. Accordingly, the mixture of precipitant solution and anti-solvent in the packed bed 102 is spread or split into very fine droplets threads or thin films in the micrometer to nanometer range, under the high gravity field created by centrifugal forces to thereby result in a high mass transfer rate and heat transfer rate between the precipitant solution and the anti-solvent. This also results in an intense micro-mixing between the precipitant solution and the anti-solvent to interact and form a highly uniformly-supersaturated mixture in a very short time (i.e. less than 10 ms) in which, nano-sized protein particles precipitate out from the mixture of precipitant solution and anti-solvent.

The magnitude of the centrifugal force exerted on the mixture of precipitant solution and anti-solvent within the packed bed 102 is dependent on the speed of rotation of the shaft 105 and the packed bed 102. The higher the speed of rotation of the shaft 105 and the packed bed 102, the larger the magnitude of the high gravity level or shear force acting on the mixture of precipitant solution and anti-solvent.

The nano-sized precipitate particles suspended in the resultant liquid medium are removed from the chamber 101 via product outlet 107.

Figure 2:
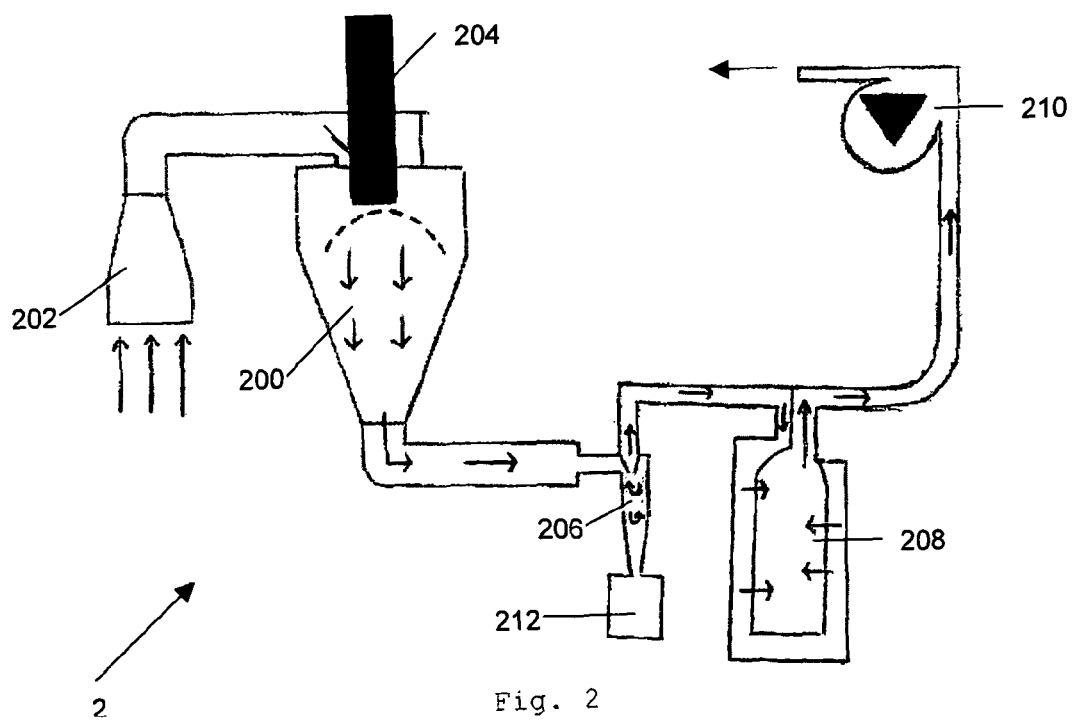
FIG. 2 shows a schematic drawing of a spray dryer for spray drying a suspension of nano-sized protein particles to make micro-sized protein particles according to one disclosed embodiment.

Referring to FIG. 2, there is shown a spray dryer 2 for spray drying a suspension of nano-sized protein particles. The spray dryer 2 comprises a drying zone 200, an air heater 202, a two-fluid nozzle atomizer 204, a cyclone separator 206, an outlet filer 208 and an aspirator 210. The drying gas is heated by an electric air heater 202 before it enters the drying zone 200. The suspension is introduced as a spray of droplets into the drying zone 200 as it exits the two-fluid nozzle atomizer 204 due to the small orifice (not shown) that is placed at the entrance of the two-fluid nozzle atomizer 204 into the drying zone 200.

In the drying zone 200, heat is transferred from the drying gas to the atomized droplets. As discussed above, it is thought that the physical properties of the spray dried micro-sized protein particles are dependent on the type of atomizers used, the inlet temperature, the amount of suspended nano-sized protein particles in the liquid medium, the residence time in the drying zone, the flow rate of the suspension, the type of solvent/anti-solvent system used during the precipitating step and direction of flow of drying gas.

As the droplets are dried, agglomeration of the nano-sized protein particles occurs to form micro-sized protein particles. The micro-sized protein particles are collected in the bottom of the drying zone 200 and are carried by the drying gas to a cyclone separator 206 that functions to separate the formed micro-sized protein particles from the drying gas. The micro-sized protein particles are collected in a collector 212 that can be detached from the cyclone separator 206 when required.

An outlet filter 208 functions to trap and hence removes fine particles that are too light to be separated in the cyclone separator 206. The outlet filter 208 removes fine particles from the drying gas before it is discharged to the atmosphere.

The aspirator 210 aids in the passage of drying gas through the drying chamber 200, cyclone separator 206, outlet filter 208 and into the atmosphere as shown by the arrows in FIG. 2.

Alternatively, an inert loop (not shown) may be used to recycle the drying gas back to the drying zone 200 instead of releasing it into the atmosphere. If nitrogen is used as the drying gas, an inert atmosphere is maintained inside the drying zone 200 and in the inert loop. The inert atmosphere is critical when spray drying flammable solvents in order to prevent the incidence of explosions. The inert loop may pass through a condenser to condense and hence recover any vapourized solvent present in the gas stream.

EXAMPLES

Non-limiting examples of the invention and a comparative example will be further described in greater detail by reference to specific Examples, which should not be construed as in any way limiting the scope of the invention.

Example 1

Micro-sized insulin particles are prepared in this example according to a disclosed process. In this process, the first step involves precipitation of nano-sized insulin particles from a precipitant solution and the second step involves spray drying of a suspension of nano-sized insulin particles that are formed from the first step.

In the first step, 1 g of rDNA insulin (at 99.2% weight/weight purity) obtained from Biocon of Bangalore, India was dissolved in 96 ml 0.01 M hydrochloric acid from Honeywell of Morristown, N.J. of the United States of America (37% weight/volume) in a beaker and mixed gently by hand. Alternatively, a magnetic stirrer at low speed, such as 50 rpm, can be used to dissolve the insulin.

After the insulin is completely dissolved in the 0.01 M hydrochloric acid, 4 ml of 2% weight/volume of ammonium acetate solution in deionized water was added and mixed gently. As mentioned above, ammonium acetate acts as a precipitation aid to initiate precipitation of the insulin in the micro-mixing step.

The total volume of the resultant solution, henceforth termed as the "precipitant solution", was 100 ml. The precipitant solution was pumped at a rate of 30 ml/min using a Syringe pump (PHD 2000 Infusion/withdraw pump) obtained from Harvard Apparatus of Holliston, Mass. of United States of America, into the liquid inlet 104a of the molecular mixing unit 100 of FIG. 1. At the same time, 900 ml of anti-solvent such as isopropanol, obtained from Tedia of Farfield, Ohio of the United States of America of 99.5% volume/volume purity, was pumped using a Watson Marlow 323 peristaltic pump at a rate of 270 ml/min into liquid inlet 104b of the molecular mixing unit 100 of FIG. 1. Therefore, the ratio of solvent:anti-solvent is 1:9.

The rotating speed of the agitator in the form of a packed bed 102 was set to 1700 rpm to enable precipitation of nano-sized insulin particles when the precipitant solution was mixed with the anti-solvent in the mixing zone 101A. The Reynolds number in the mixing zone 101A is about 4000, indicating a high level of turbulence. The turbulent conditions in the mixing zone 101A aids in intimate mixing of the precipitant solution and the anti-solvent in a short period of time, typically within a few seconds, or more particularly, less than 1 second. Here, the total amount of time after addition of the precipitant solution and the anti-solvent into the molecular mixing unit 100 (total volume=1000 ml), precipitation and collection of the resultant nano-sized insulin particles was about 3 minutes. The nano-sized insulin particles obtained after precipitation was collected from the chamber 101 via outlet conduit 107 using a beaker.

Figure 3:
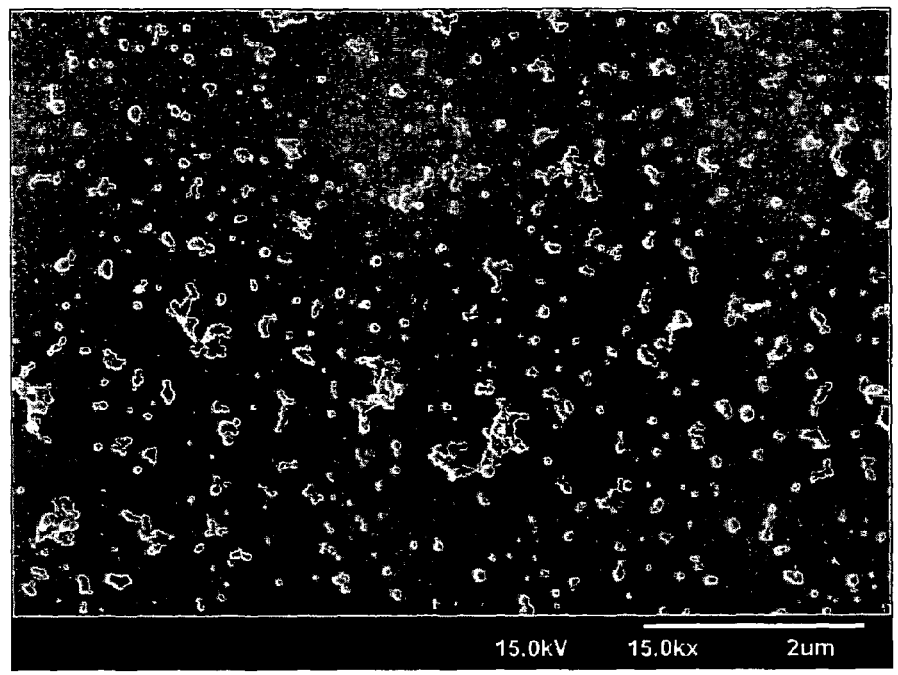
FIG. 3 is a Field Emission gun Scanning Electron Microscopic (FESEM) image obtained at 15000× magnification of nano-sized insulin particles obtained from the molecular mixing unit of FIG. 1.

FIG. 3 is a FESEM image obtained at 15000× magnification of nano-sized insulin particles obtained from this step. The nano-sized insulin particles were dropped onto a copper grid that serves as a support for the SEM image. FIG. 3 shows the individual nano-sized insulin particles that are formed in the molecular mixing unit 100. Some of the nano-sized insulin particles may clump together during sampling but are usually dispersed from each other. The mass median diameter ($D_{50}$) of the nano-sized insulin particles is about 362 nm, the steepness ratio is about 1.62 and the span value is about 1.12. Hence, FIG. 3 shows that the nano-sized insulin particles obtained have a relatively narrow particle size distribution.

Figure 4:
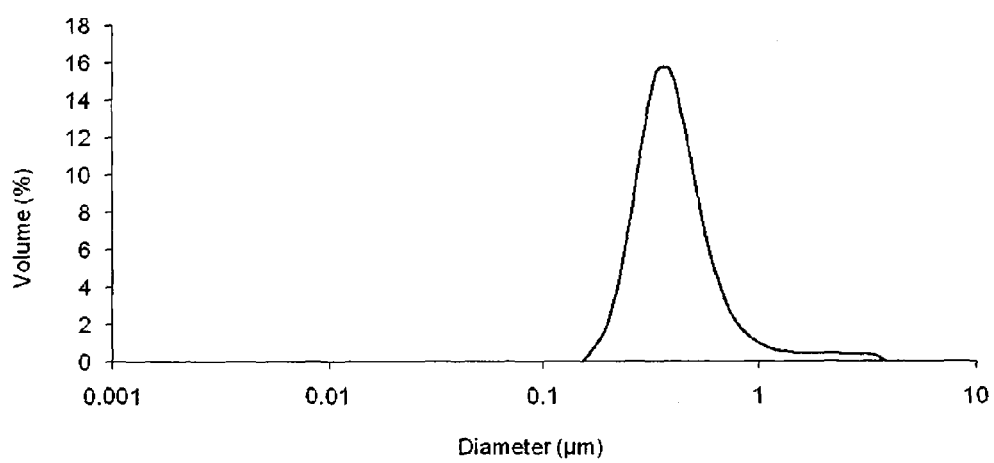
FIG. 4 is a graph of the size distribution of the nano-sized insulin particles. The y-axis indicates the percentage of nano-sized insulin particles (volume %) that corresponds to the diameter (in μm) on the x-axis.

FIG. 4 is a graph of the size distribution of the nano-sized insulin particles, obtained from a Dynamic Light Scattering particle size analyzer. Here, a 4 ml sample of a suspension of nano-sized insulin particles in the liquid medium was placed in a quartz cell and the particle size was measured using a HORIBA™ LB550 DLS particle size analyzer obtained from HORIBA, Ltd of Japan. The refractive index of insulin was taken as 1.56 and the refractive index of isopropanol was taken as 1.36. As seen in FIG. 4, the y-axis indicates the percentage of nano-sized insulin particles (volume %) that corresponds to the diameter (in μm) on the x-axis. The mean particle size of the nano-sized insulin particles in suspension is about 360 nm.

The nano-sized insulin particles suspended in the liquid medium collected in the beaker was connected to a tubing that leads into the two-fluid nozzle atomizer 204 of the spray dryer 2. A BUCHI™ 290 laboratory scale spray dryer 2 obtained from BUCHI Labortechnik AG of Switzerland as shown in FIG. 2 was used. The parameters of the BUCHI™ 290 laboratory scale spray dryer 2 was set as follows: inlet temperature of the drying gas was 70° C.; rate of drying gas flow through the spray dryer 2 as controlled by the aspirator 210 was 40 m³/hr; liquid flow rate of the suspension through the two-fluid nozzle atomizer 204 was 8 ml/min; compressed gas (nitrogen gas) flow rate through the two-fluid nozzle atomizer 204 to atomize the suspension was 670 L/hr; inert loop temperature was set at −10° C. The outlet temperature was measured to be 35° C.

In the spray dryer 2, the nano-sized insulin particles agglomerate in the drying zone 200 to form micro-sized insulin particles. The micro-sized insulin particles are separated from the drying gas in the cyclone separator 206 and collected in the collector 212. The time taken to dry 1000 ml of suspension in the spray dryer 2 is about ~2 hours.

The micro-sized insulin particles collected are placed in a vacuum oven set at 30° C. to remove excess ammonium acetate and other ammonium salts by sublimation. It is also possible to remove excess ammonium acetate and ammonium salts prior to spray drying by washing the suspension of nano-sized insulin particles obtained after the precipitation step.

Figure 5:
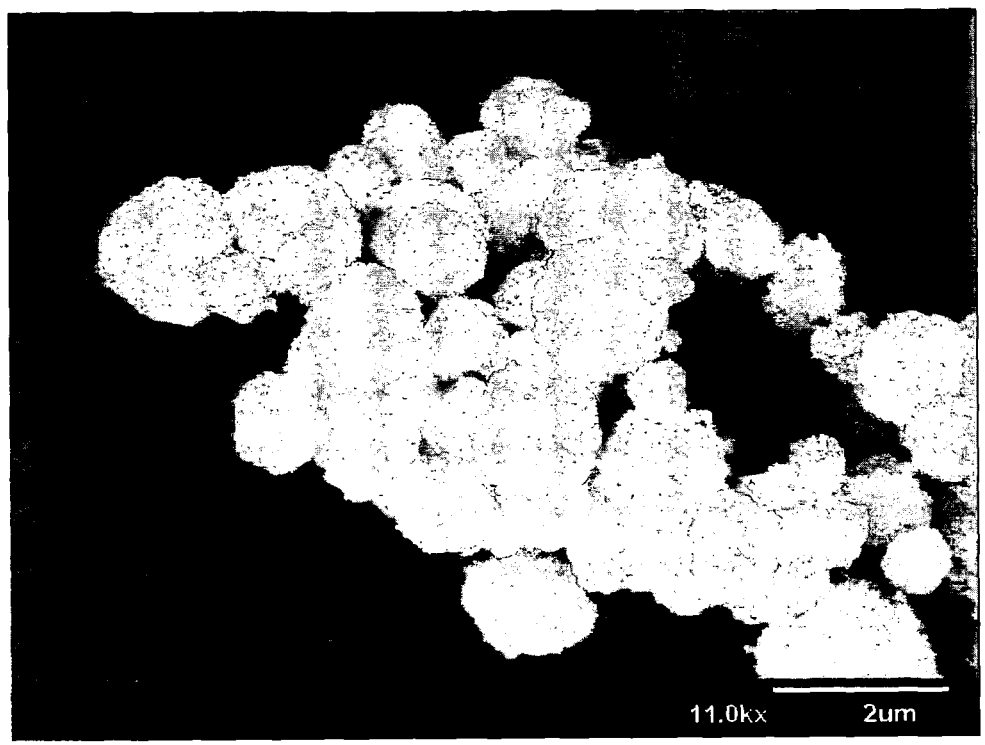
FIG. 5 is a FESEM image at 11000× magnification of a plurality of micro-sized insulin particles made according to a disclosed embodiment.
Figure 6:
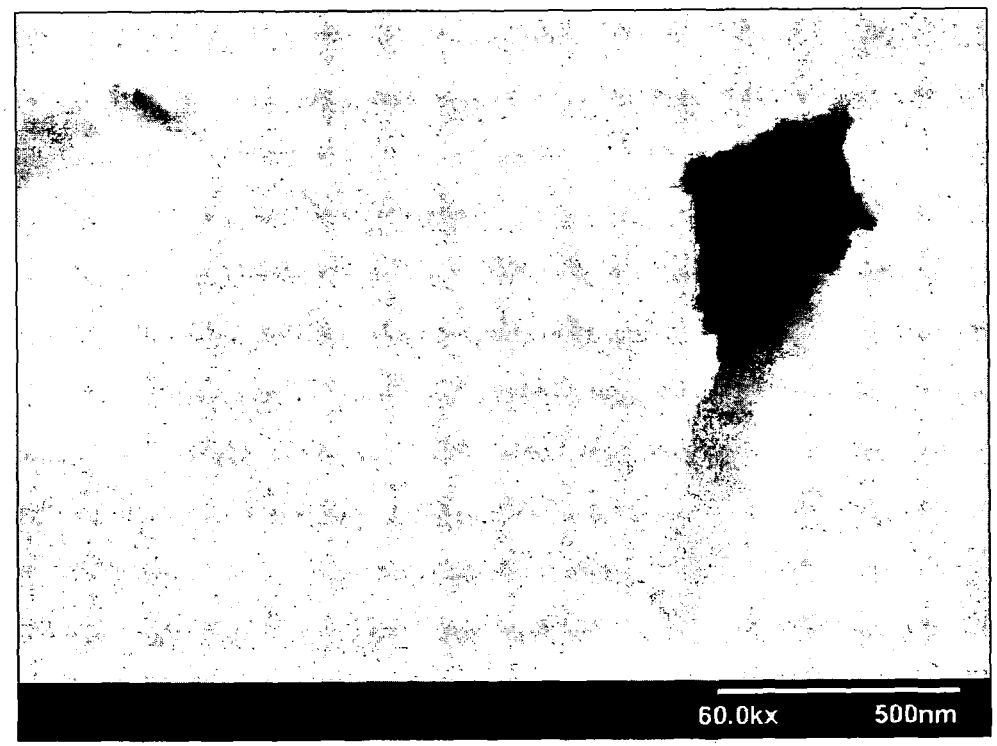
FIG. 6 is a FESEM image at 60000× magnification of the plurality of micro-sized insulin particles of FIG. 5.

FIG. 5 and FIG. 6 show FESEM images at respective magnification of 11000× and 60000× of micro-sized insulin particles after the spray drying step. It can be seen that the micro-sized insulin particles are an agglomerate of a plurality of nano-sized insulin particles. As discussed above, it is thought that agglomeration occurs during the drying step as a result of the surface tension exerted on the nano-sized insulin particles at the liquid/gas interface of the shrinking (evaporating) droplets.

Furthermore, FIG. 6 shows that the surfaces of the micro-sized insulin particles are uneven and rough such that individual particles do not substantially stick to each other easily. When insulin particles clump together, an increase in the diameter of the resultant particle means that the bigger particle is not efficiently delivered to the lungs as compared to smaller, individual insulin particles that have a smaller diameter. Accordingly, the micro-sized insulin particles as disclosed herein do not substantially clump together during pulmonary delivery. This is advantageous during aerosolization of the micro-sized insulin particles when they are released from a pulmonary delivery device into the lungs of a patient.

Figure 7:
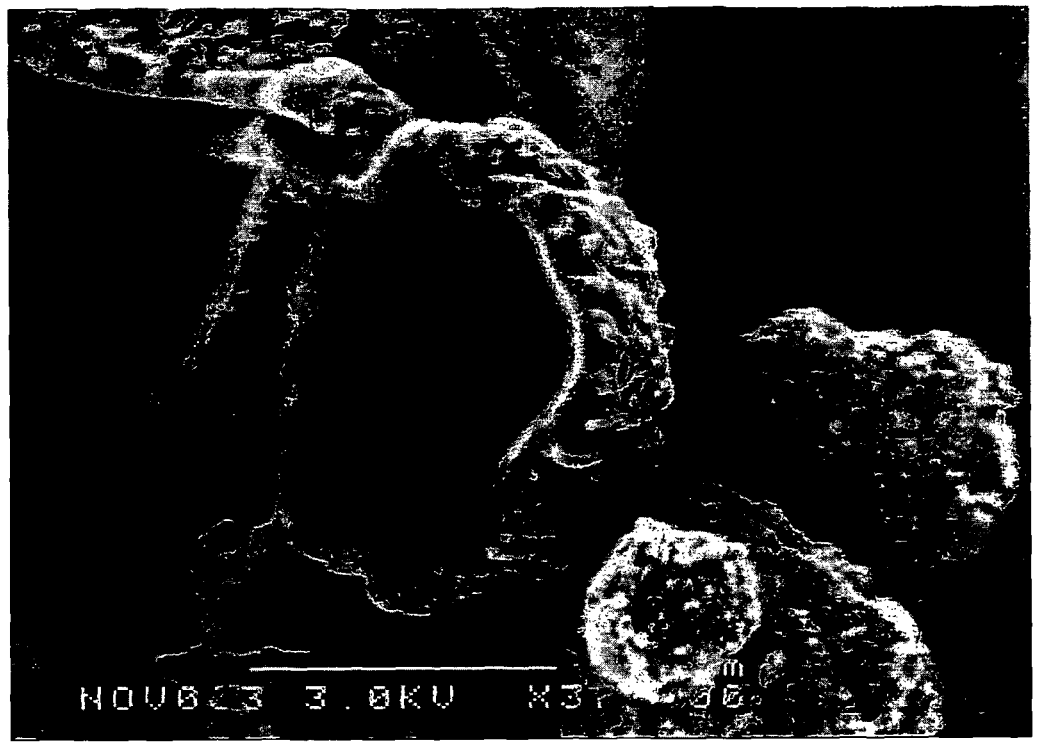
FIG. 7 is a FESEM image at 37000× magnification of a micro-sized insulin particle from FIG. 5 that has been cut using a focused ion beam.

FIG. 7 is a FESEM image at 37000× magnification of a micro-sized insulin particle that has been cut open using focused ion beam milling. FIG. 7 shows that the inner core of the micro-sized insulin particles is a void. As discussed above, the conditions during the spray drying step aid in the creation of a void in the inner core of the micro-sized insulin particles. Due to the presence of a void in the inner core of the micro-sized insulin particles, the micro-sized insulin particles have a high porosity value (about 50-60%) and low density of about 0.3 g/cm³.

The micro-sized insulin particles have a mass median aerodynamic diameter of about 2.31 μm. The mass median aerodynamic diameter is important when the micro-sized insulin particles are delivered via pulmonary delivery devices, such as inhalers and nebulizers, as the mass median aerodynamic diameter is one of the factors that determines the residence time and deposition of the micro-sized insulin particles into the lungs of a patient.

Figure 8:
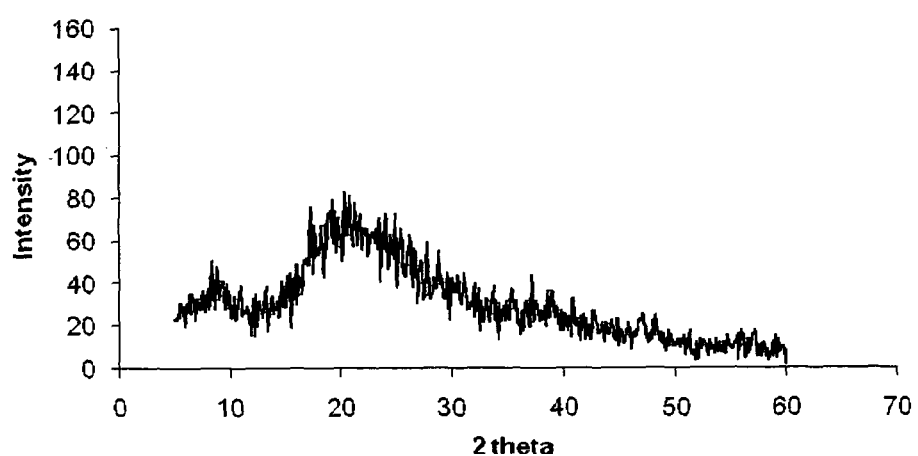
FIG. 8 is a diffraction pattern of the micro-sized insulin particles of FIG. 5 obtained via X-ray diffraction.

FIG. 8 is a diffraction pattern of the micro-sized insulin particles of FIG. 5 obtained via X-ray diffraction. Approximately 100 mg of dried, powdered micro-sized insulin particles was mounted on a stage and placed inside an X'pert Philips™ X-Ray Diffractometer obtained from Philips in the Netherlands. The scan was performed using a scan angle between 5 to 60, a step size of 0.1, a detection slit of 0.5, a mask of 150 mm, a receiving slit of 1, a scan speed of 0.1 and a time/step of 1. As seen in FIG. 8, a typical amorphous halo was observed in the x-ray diffraction pattern of the micro-sized insulin particles. This indicates that the micro-sized insulin particles are essentially amorphous in nature.

Example 2

Comparison between Insulin Particles Obtained from Example 1 and Unprocessed Insulin Obtained from the Supplier A series of experimental analyses and tests are carried out to compare the physical properties of micro-sized insulin particles (herein termed as "HGCP insulin") prepared according to Example 1 with unprocessed insulin (herein termed as "raw insulin") that was obtained from the above supplier, Biocon, without any treatment or modifications. The batch used to process the "HGCP insulin" is the same as that for the "raw insulin".

Fourier Transform Infra-red Spectrometry

Figure 9:
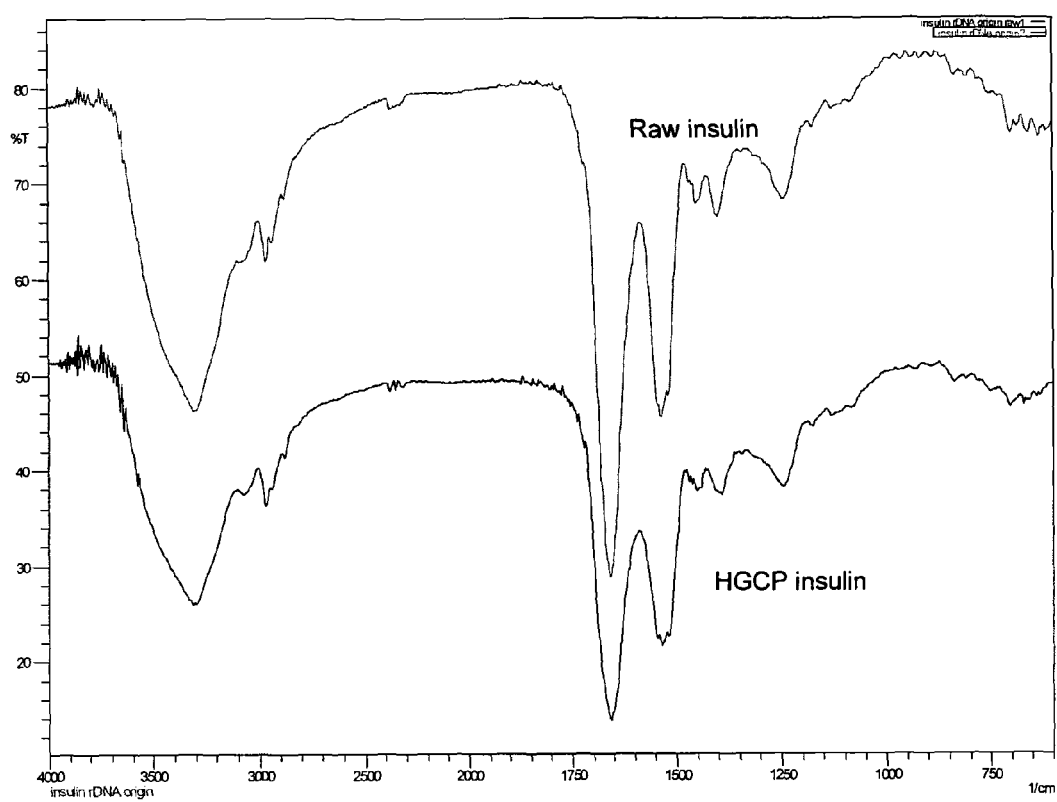
FIG. 9 is a Fourier Transform Infra-red (FTIR) Spectrum showing a comparison between unprocessed insulin and the micro-sized insulin particles of FIG. 5.

FIG. 9 is a FTIR spectrum of the "HGCP insulin" and the "raw insulin". Approximately 200 mg of potassium bromide (KBr) was added to a motor and ground finely. Following which, 2 mg of each test insulin ("HGCP insulin" and the "raw insulin") was added and gently grinded to allow for complete mixing to form a uniform blend. KBr is a matrix which is used to dilute the insulin sample and form a thin disc for the FTIR characterization. The thin disc can be formed using a KBr press. If KBr is not used, a thin disc will not form and the absence of the thin disc will consequently overload the detector signal. KBr has been used here because it has no significant infra-red absorption in the range studied. The KBr/insulin film was then loaded into a holder and mounted inside the FTIR (IRprestige 21 obtained Shimadzu Corporation of Japan) and used on the transmission mode. FIG. 9 indicates that the FTIR spectrum of the "raw-insulin" and the "HGCP insulin" was similar, hence indicating that the chemical integrity and the secondary structure are substantially similar.

UV Spectrometry

Figure 10A:
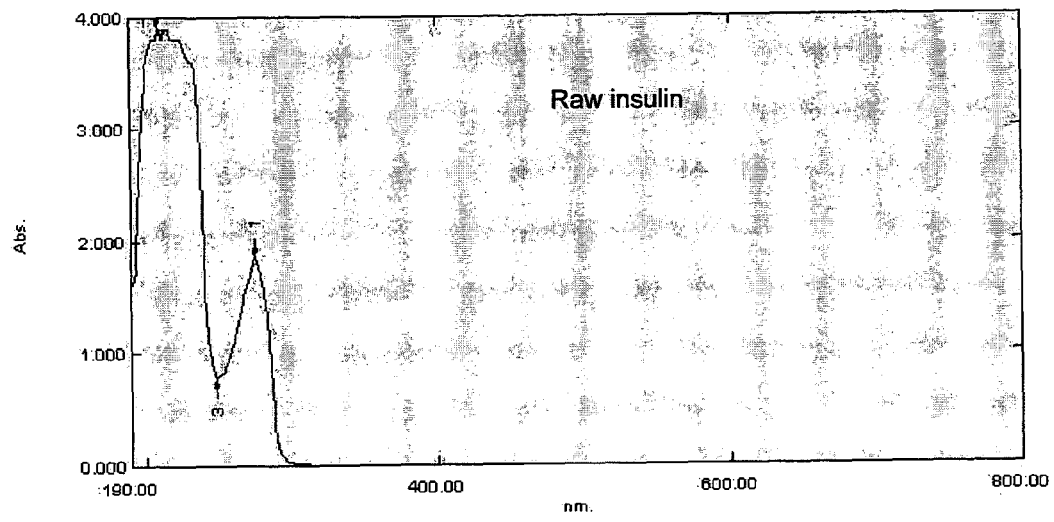
FIG. 10A is a UV spectrum of the unprocessed insulin.
Figure 10B:
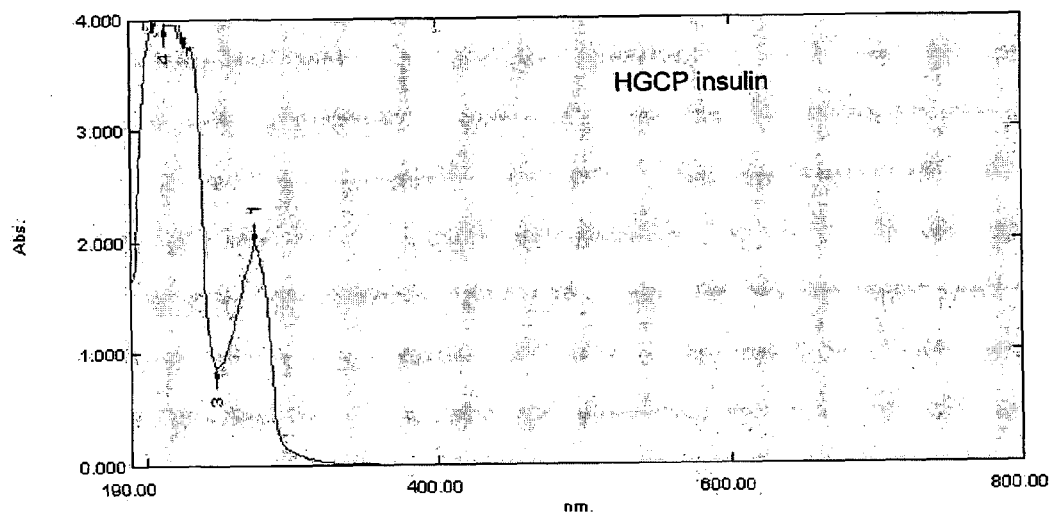
FIG. 10B is a UV spectrum of the micro-sized insulin particles of FIG. 5.

FIG. 10A indicates the UV spectrum of the "raw insulin" while FIG. 10B indicates the UV spectrum of the "HGCP insulin". Approximately 10 mg of test insulin was dissolved into 5 ml of 0.01M hydrochloric acid and the UV-V is spectrum was scanned over the range 190 to 800 nm. The UV instrument (Model 2450 obtained from Shimadzu Corporation of Japan) was operated in the dual beam mode. FIG. 10A and FIG. 10B indicate that no spectral scattering in the visible region was detected, indicating that no molecular aggregation of the "HGCP insulin" occurred during the precipitating step and the drying step.

Circular Dicroism Spectrometry

Figure 11:
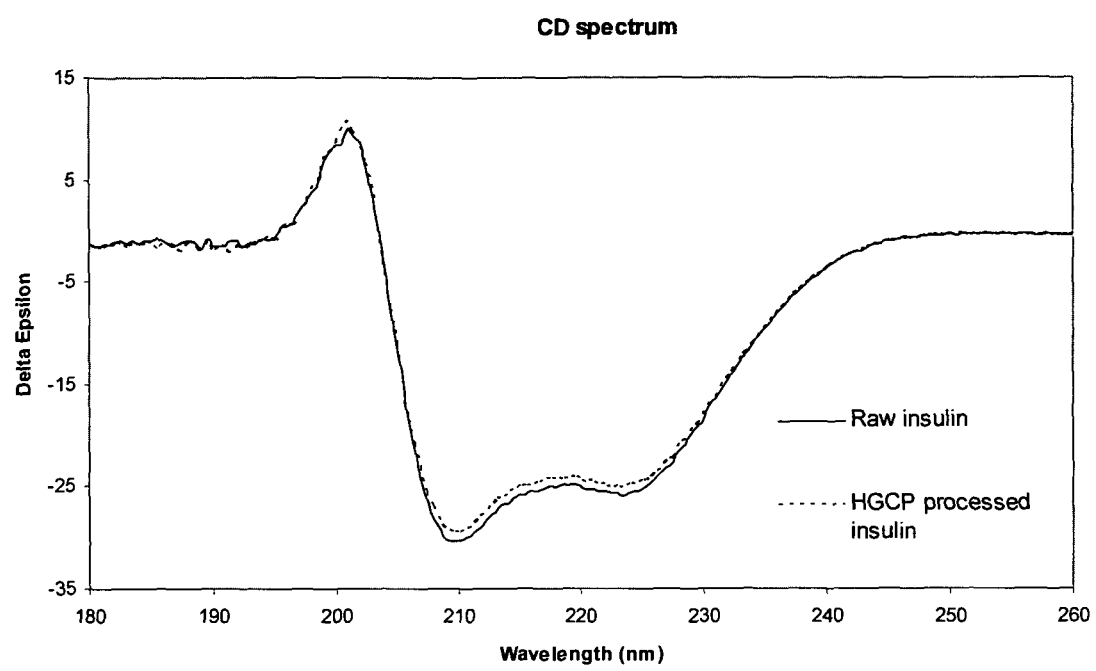
FIG. 11 is a Circular Dicroism (CD) image showing a comparison between unprocessed insulin and the micro-sized insulin particles of FIG. 5.

FIG. 11 indicates the CD spectrum of the "raw insulin" and the "HGCP insulin". A Chirascan CD spectrometer from Applied Photophysics of Surrey of the United Kingdom was used here. Each of the test insulin was dissolved in 0.01 N hydrochloric acid (5 mg/ml). 60 μl sample solution was loaded to the cuvette (0.1 mm path length) and was scanned at ambient temperature from wavelength 180 to 260 nm. The scans were obtained at bandwidth of 1 nm, step size of 0.5 and time per step of 3 s. The data was converted to .txt file using APDataconverter. Deconvolution of the spectrum was performed using CDNN software and the percentage of alpha-helix and random coil were given. The spectrum obtained is shown in FIG. 11. The spectrum from 180-190 nm was noisy and so the results from 190-260 nm were given in the following Table 1.

TABLE 1

|  | Raw insulin | HGCP processed insulin |
| --- | --- | --- |
| α-helix | 97.2% | 96.8% |
| Random coil | 0.6% | 0.8% |

Table 1 indicates that substantially similar spectrum was observed for each sample. Both the "raw insulin" and the "HGCP insulin" are predominantly composed of α-helix. No significant difference was found between the "raw insulin" and "HGCP insulin". Therefore, the data implies that the secondary structure of the insulin is maintained throughout the micro-mixing step and the spray drying step.

Reverse Phase HPLC

Figure 12:
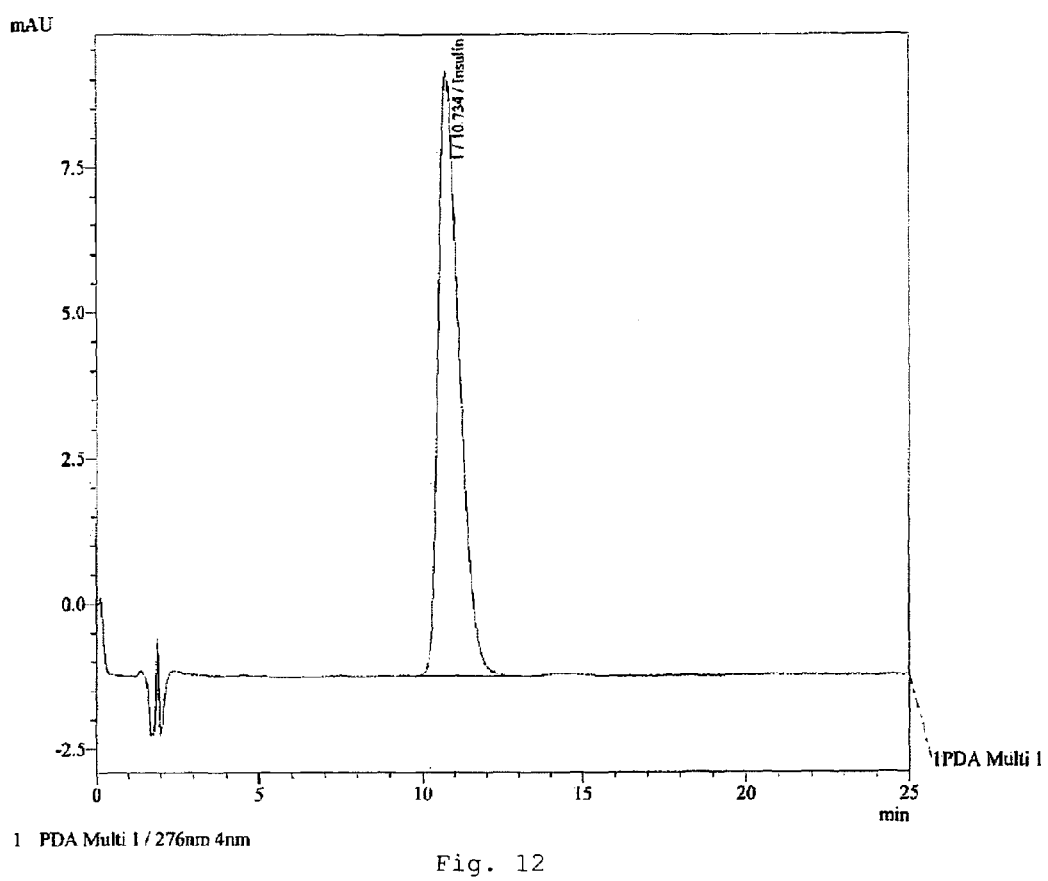
FIG. 12 is a chromatogram of the micro-sized insulin particles of FIG. 5 obtained via reverse phase High Performance Liquid Chromatography (HPLC).
Figure 13:
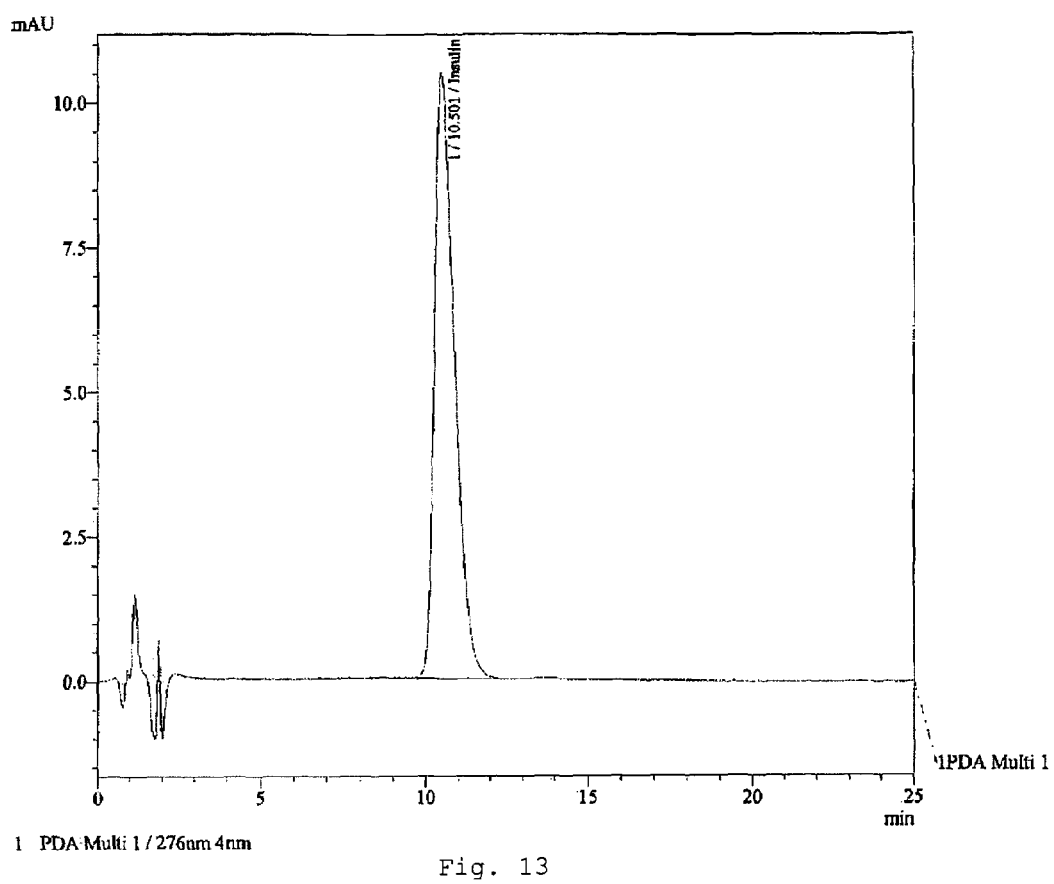
FIG. 13 is a chromatogram of unprocessed insulin obtained via reverse phase HPLC.

FIG. 12 and FIG. 13 indicate the HPLC chromatogram of "HGCP insulin" and "raw insulin" respectively. Reverse phase HPLC is used to determine the level of deamido insulin (A21) that indicates the degradation of insulin via deamidation. The reverse phase HPLC process was set as follows:

Mobile phase:
Solvent A 0.1% TFA in acetonitrile (Riedel de-Haen part number 34976)
Solvent B 0.1% TFA in $H_2O$ (Riedel de-Haen part number 34978)
Premix solvent ratio in online mixer
Solvent A:Solvent B
29:71
Flow rate: 0.4 ml/min
Analytical Column: Jupitor Proteo C18 150×2 mm A (Phenomenex part number 00E-4396-BO)
Column temperature: 30° C.
Injection volume: 10 μl
Detector: UV set to 276 nm FIG. 12 and FIG. 13 indicate that the "HGCP insulin" and the "raw insulin" do not show evidence of the deamido insulin A21.

Size Exclusion Chromatography

Figure 14:
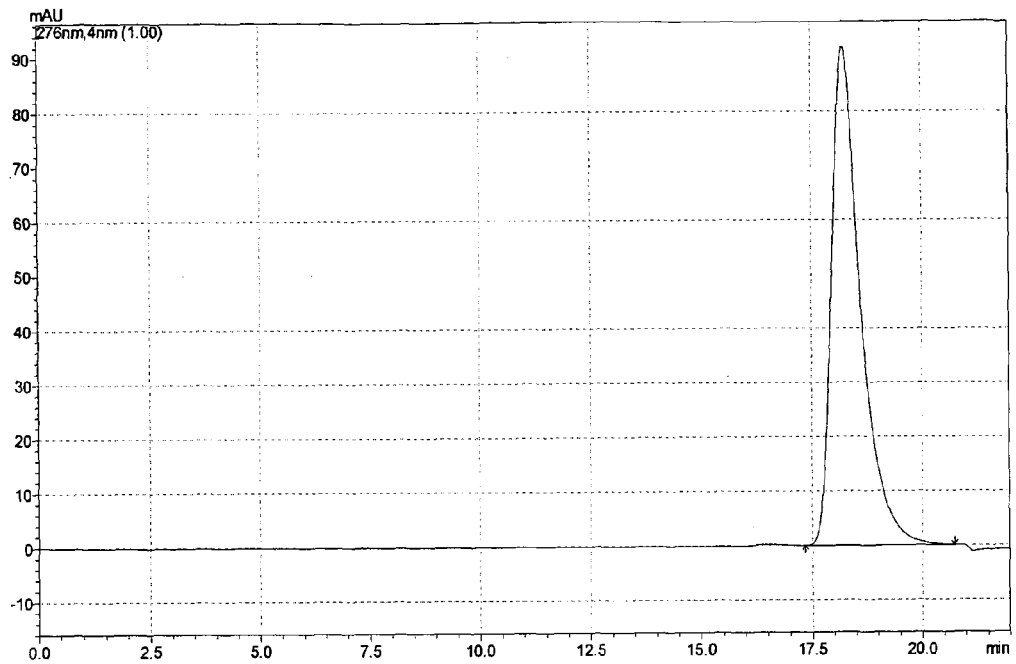
FIG. 14 is a chromatogram of the micro-sized insulin particles of FIG. 5 obtained via size exclusion chromatography (SEC) using a gel permeation column.
Figure 15:
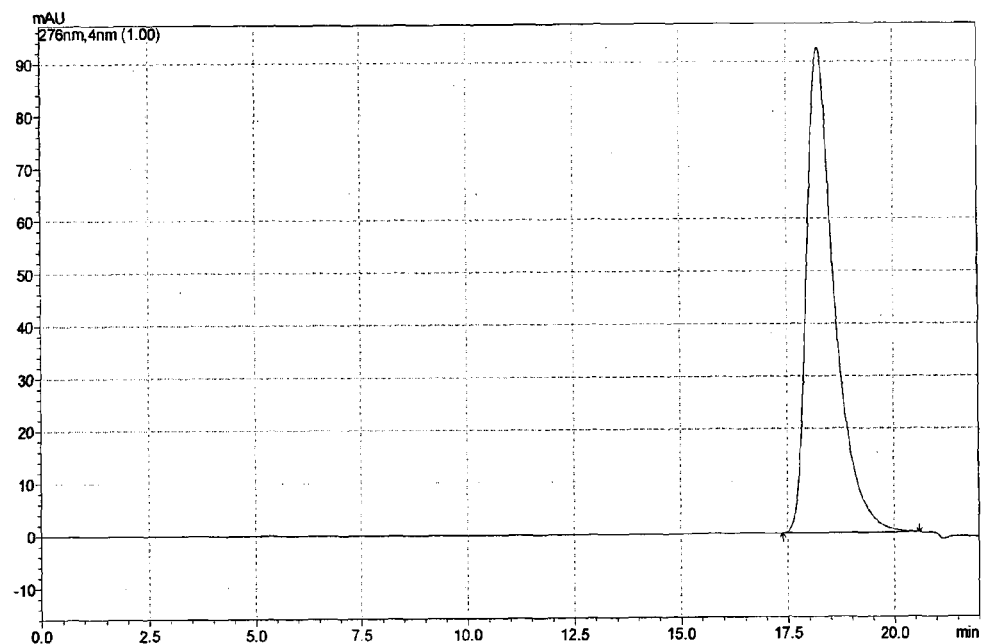
FIG. 15 is a chromatogram of unprocessed insulin obtained via SEC using a gel permeation column.

FIG. 14 and FIG. 15 indicate the SEC chromatogram of "HGCP insulin" and "raw insulin" respectively. SEC was used to determine the extent of molecular aggregation and/or protein polymerization.

Approximately 40 mg of "HGCP insulin" and "raw insulin" was added into a 10 ml volumetric flask. 0.1 M HCl was used to dissolve the insulin and the total volume of the solution was set to 10 ml. The solutions were prepared fresh and injected into the HPLC of the size exclusion chromatography type. The conditions of the HPLC was as follows:

Mobile Phase: 0.1% L-Arginine solution:Acetonitrile:Glacial acetic acid Premixed in ratio 65:20:15)
Analytical Column: Insulin HMWP column 7.8×300 mm (Waters part number WAT201549)
Column temp: 40° C.
Injection Vol: 20 μL
Pump Flow rate: 0.5 mL/min
Detection: UV set to 276 nm FIG. 14 and FIG. 15 indicate that both test insulin solutions give one distinct peak at a retention time of 18.3 minutes. This is attributed to the insulin monomer. Hence, it is shown that the molecular structure of insulin prepared according to a disclosed embodiment is substantially similar to that of unprocessed or raw insulin obtained directly from the supplier.

Figure 16:
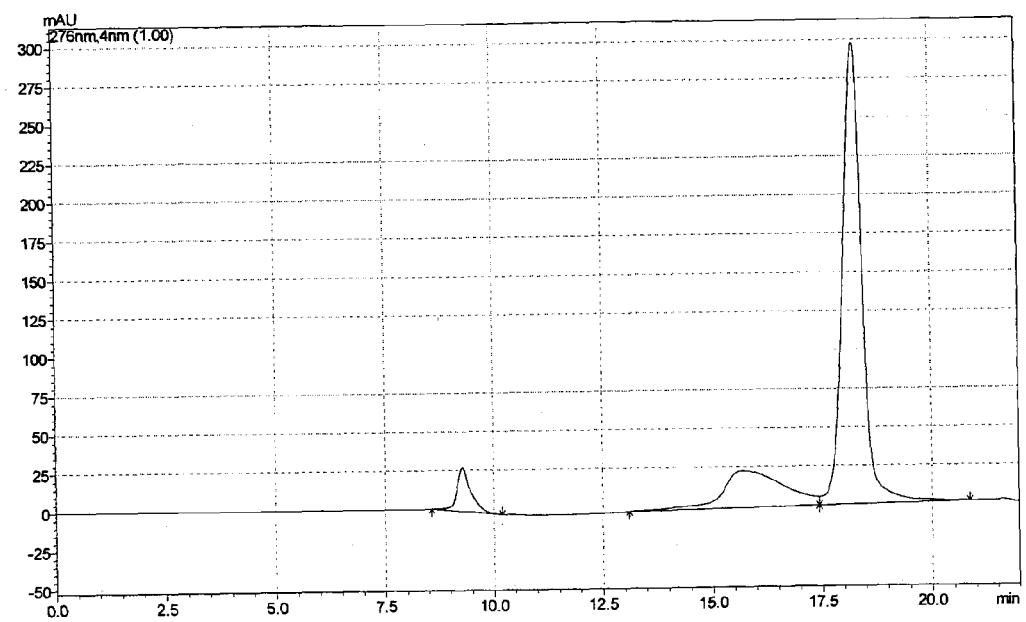
FIG. 16 is a chromatogram of "stressed" unprocessed insulin obtained via SEC using a gel permeation column.

A characteristic chromatogram of insulin aggregation is shown in FIG. 16. FIG. 16 is a chromatogram of a solution of "raw insulin" that had been prepared 1 month ago and stored at room temperature. The dimer formation is evidenced by a peak at retention time of 15.7 minutes and formation of a complex polymeric structure is evidence by a peak at a retention time of 9.3 minutes. These peaks are absent from FIG. 14, indicating that dimer formation and complex polymeric structure are absent in the insulin prepared according to the disclosed process.

The experimental data obtained in this example indicates that "HGCP insulin" has substantially similar properties to that of "raw insulin", indicating that the steps of precipitating and drying the processed insulin do not substantially affect the chemical integrity, secondary structure, molecular aggregation or degradation of the final insulin product.

Comparative Example 1

Insulin Powder Obtained from Spray Drying an Insulin Solution

An insulin solution was prepared by dissolving 1 g of rDNA insulin obtained from the same supplier, Biocon, as above in 1000 ml 0.01 M hydrochloric acid using mixing as defined in Example 1.

The insulin solution obtained was spray dried using a BUCHI™ 290 laboratory scale spray dryer 2 obtained from BUCHI Labortechnik AG of Switzerland as shown in FIG. 2 with the same parameters as in Example 1.

Reverse Phase HPLC

Figure 17:
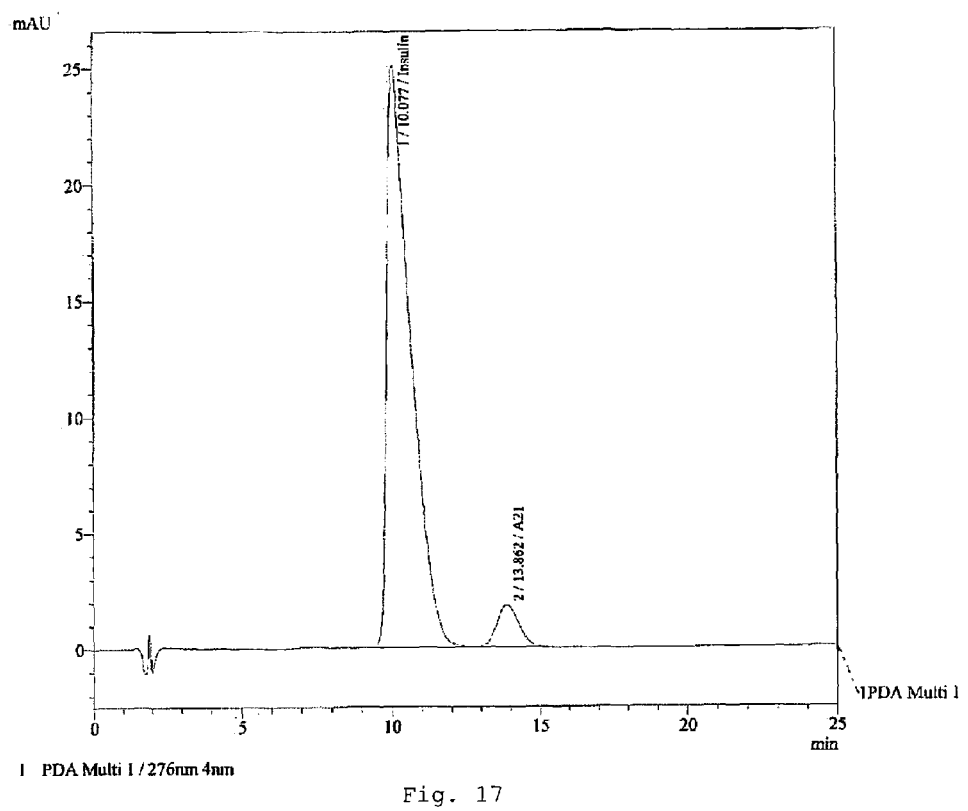
FIG. 17 is a chromatogram of unprocessed insulin obtained via reverse phase HPLC. The unprocessed insulin is stored at room temperature for 2 days.
Figure 18:
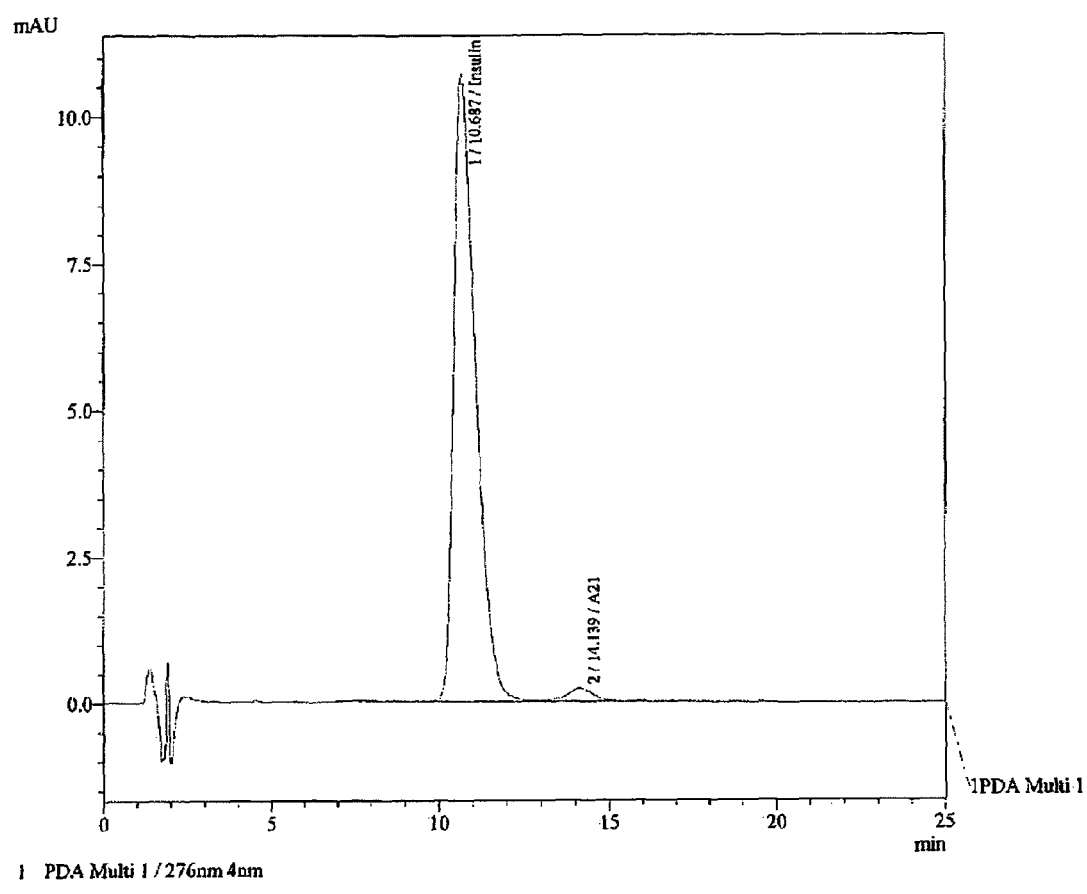
FIG. 18 is a chromatogram of insulin particles that are obtained in Comparative Example 1.

FIG. 18 is the HPLC chromatogram of insulin particles obtained in this comparative example 1. The reverse phase HPLC experiment is carried out with the same instrument and parameters as FIG. 12 and FIG. 13. There is evidence of deamido insulin formation during the process of spray drying an insulin solution directly as seen from the A21 peak at the 14.1 minute value. This degradation is similar to a situation where raw insulin is stored under adverse conditions as shown in FIG. 17. Here, raw insulin is stored in 0.01 M hydrochloric acid at room temperature for 2 days. As shown in FIG. 17, degradation of the insulin occurs after it has been stored at room temperature for 2 days as shown by the presence of an A21 peak that occurs at the 14 minute value.

Hence, it can be seen that the process of spray drying an insulin solution directly (Comparative Example 1) results in a greater degree of insulin degradation when compared to a process of precipitating nano-sized insulin particles from a precipitant solution and spray drying the suspension obtained (Example 1).

Without being bound by theory, it is believed that insulin degradation is due to one or both of the following conditions. Firstly, the high physical shear forces experienced by the insulin solution as it passes through the nozzle atomizer of the spray dryer stresses and hence degrades the insulin molecules. When insulin is in solution, the insulin molecules can Move about freely. The mobility of the insulin molecules increases the degradation kinetics and hence, more degradants are created. This is in contrast to the process disclosed herein whereby when nano-sized insulin particles are spray dried, due to the rigidity of the particles suspended in the liquid medium, the suspended insulin particles are less mobile as compared to insulin molecules dissolved in solution. Secondly, the high temperatures inside the spray dryer can also contribute to insulin degradation when an insulin solution is spray dried directly.

Comparison between Insulin Powder and Insulin Powder Blends Obtained from the Process of Example 1 with Insulin Powder Obtained from the Process of Comparative Example 1

Aerosol Dispersion Analysis

Micro-sized insulin particles obtained from the process of Example 1 in the powder form, termed as "HGCP insulin" were blended with inhalation grade lactose obtained from Friesland Foods Domo from the Netherlands (LH100) in "HGCP insulin" to lactose ratios of 1:2 and 1:5 and mixed using a glass scintillation vial. This is termed as "HGCP/lactose blend 1:2" and "HGCP/lactose blend 1:5" respectively. The vial was capped and gently inverted several times to slowly mix the powder and this was followed by vortex mixing.

Figure 19:
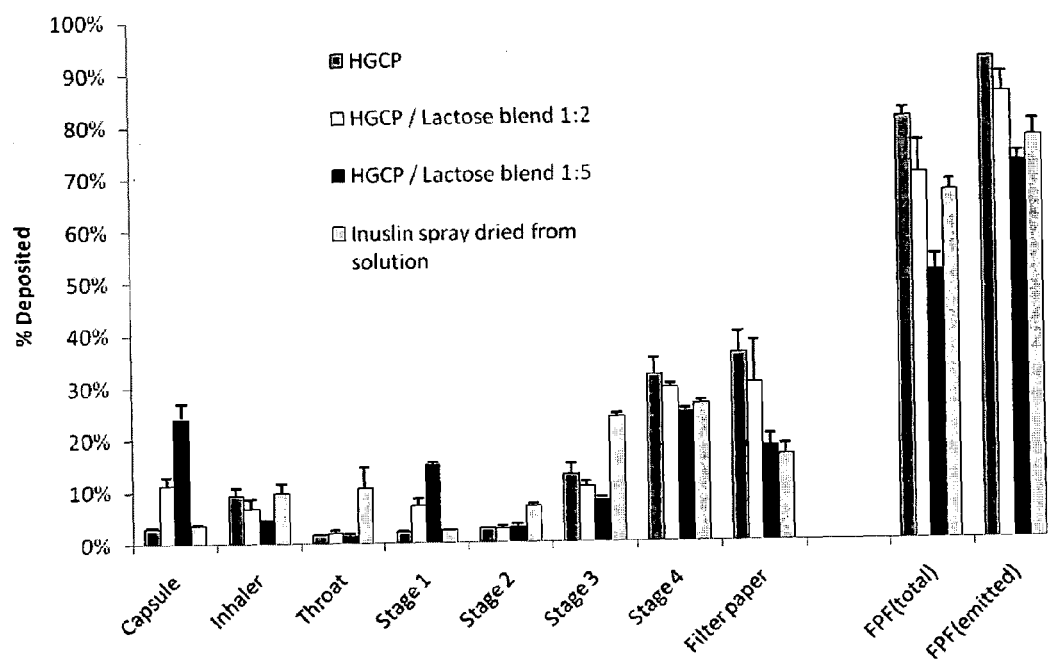
FIG. 19 shows the aerosol dispersion results of four types of aerosols produced from micro-sized insulin particles of FIG. 5, micro-sized insulin particles of FIG. 5 blended with lactose at different ratios and insulin particles that are obtained from Comparative Example 1.
Figure 20:
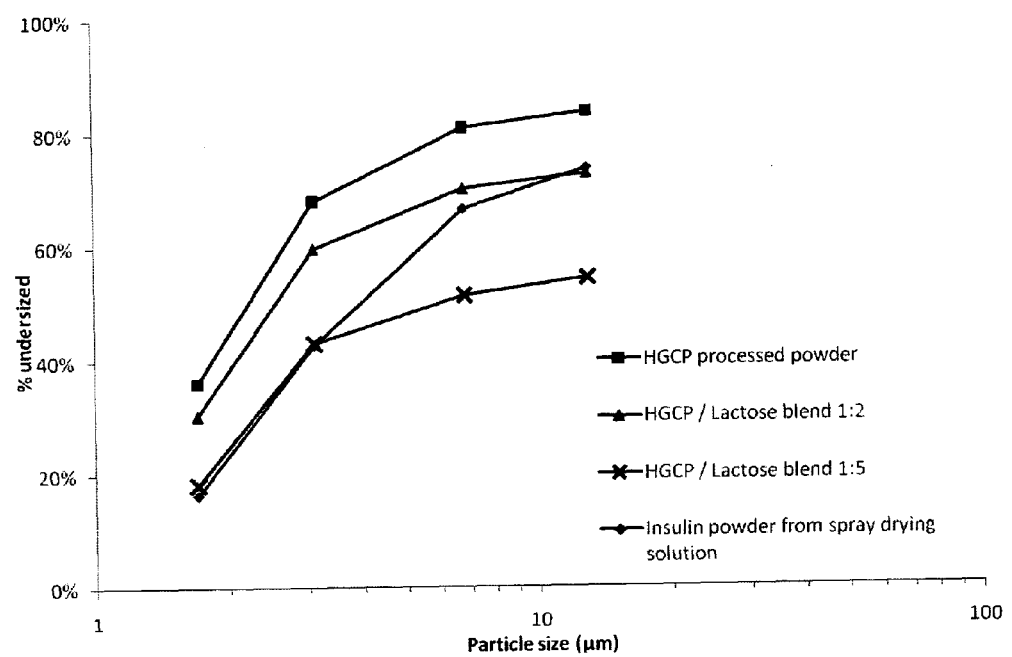
FIG. 20 is a particle size distribution of four types of aerosols produced from micro-sized insulin particles of FIG. 5, micro-sized insulin particles of FIG. 5 blended with lactose at different ratios and insulin particles that are obtained from Comparative Example 1.

Approximately 15 mg of powder of "HGCP insulin", "HGCP/lactose blend 1:2", "HGCP/lactose blend 1:5" and insulin obtained from Comparative Example 1 (herein termed as "insulin sprayed dried from solution") was loaded into individual capsules (Capsurgel from USA) and dispersed at 60 L/min using an RS01 Mod 7 Monodose Inhaler (Plastiape S.p.A of Italy). A multistage liquid impinge (MSLI) from Copley scientific of the United Kingdom was used to characterize the particle size distribution of the aerosol. In FIG. 19, the % FPFtotal shows that the insulin powder obtained from the process of Example 1 ("HGCP insulin", "HGCP/lactose blend 1:2", "HGCP/lactose blend 1:5") has a significant increase over insulin powder obtained from spray drying an insulin solution directly ("insulin sprayed dried from solution"). Good aerosol performance is retained even with the addition of lactose. FIG. 20 shows that the particle size distribution of the aerosol produced from "HGCP insulin" and the "HGCP/lactose blend 1:2" have significantly smaller aerodynamic sizes compared to that of the insulin powder obtained from spray drying an insulin solution directly.

Applications

Advantageously, the disclosed process forms micro-sized protein particles that are suitable for use in an inhalation device for pulmonary delivery to a patient. This can be particularly useful for delivery of insulin particles in an aerosol formulation for the treatment of patients suffering from diseases which relate to insulin.

Advantageously, the micro-sized protein particles may be porous which means that they have a lower density as compared to particles of the same physical size, rendering the particles lighter and therefore suitable for use in inhalation devices for pulmonary delivery to a patient.

More advantageously, the micro-sized protein particles may have a void in their inner core. The void may be formed by the agglomeration of the nano-sized protein particles in the drying step, such as in the spray drying step. This void renders the particles relatively light compared to particles of like physical size which do not have a void. Without being bound by theory, it is postulated that the void is formed by the fact that the nano-sized protein particles have a relatively narrow particle size distribution. This means that during a drying step, such as spray drying, the nano-sized protein particles are caused to bind together in a very quick period of time, leaving a void in the centre of the agglomerated particles. Advantageously, the nano-sized protein particles may be made in a high shear environment so that upon precipitation, the nano-sized protein particles are all of relatively uniform size (narrow particle size distribution).

The disclosed process may overcome some of the disadvantages of the prior art. The micro-sized protein particles have been found to retain substantially similar biological activity during either the spray drying step or the precipitation step under shear conditions when compared to unprocessed protein. Accordingly, excipients, binders and stabilizers are not required to retain the biological activity of the proteins made according to a disclosed embodiment.

As the nano-sized protein particles are formed first before the drying step, the disadvantages associated with precipitation during spray-drying or spray-freeze-drying are overcome. Furthermore, the micro-sized protein particles have been found to have less biological and/or chemical degradation as compared to protein particles obtained from spray-drying a protein solution directly.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A process of making micro-sized protein particles comprising the steps of:
    precipitating nano-sized protein particles from a precipitant solution under conditions to form a suspension of nano-sized protein particles in a liquid medium, said nano-sized protein particles having a narrow particle size distribution with a span value of less than 3; and
    spray-drying the nano-sized protein particles suspension under conditions to agglomerate the nano-sized protein particles and thereby form micro-sized protein particles having a porous structure, wherein the micro-sized protein particles are suitable for use as a formulation for pulmonary delivery.

2. The process of making micro-sized protein particles as claimed in claim 1, wherein said precipitating step comprises the step of micro-mixing a precipitant solution and an anti-solvent.

3. The process of making micro-sized protein particles as claimed in claim 1, wherein said protein is selected from the group consisting of insulin, albumin, parathyroid hormone, gonadotropin-releasing hormone, DNAse, cyclosporin, immunoglobulin, erythropoietin, interferon, colony stimulating factor, growth hormone, luteinising-hormone releasing hormone (LHRH) analog, LHRH antagonist, tissue plasminogen activator, somatostatin analog, r Factor VIII, r Factor IX, calcitonin, abciximab, dornase alfa, bone inducing protein, bone morphogenic protein, brain derived growth factor, gastrin 17 immunogen, interleukins, polymerase enhancing factor superoxide, chimeric monoclonal antibody, permeability increasing protein-21, platelet derived growth factor, stem cell factor, recombinant human thyrotropin alfa, somatomedin C and mixtures thereof.

4. The process of making micro-sized protein particles as claimed in claim 1, wherein said suspended nano-sized protein particles in said liquid medium is atomized to form droplets during said spray-drying step.

5. The process of making micro-sized protein particles as claimed in claim 4, wherein the time taken to dry said droplet is less than 10 seconds.

6. The process of making micro-sized protein particles as claimed in claim 1, wherein said suspended nano-sized protein particles have a % solids concentration in the range of 0.1% to 10% in said liquid medium.

7. The process of making micro-sized protein particles as claimed in claim 1, wherein the temperature of said suspended nano-sized protein particles is in the range of 4° C. to 40° C.

8. The process of making micro-sized protein particles as claimed in claim 1, wherein said nano-sized protein particles have a particle size in the range of 50 nm to 500 nm.

9. The process of making micro-sized protein particles as claimed in claim 2, wherein said micro-mixing is undertaken under high shear conditions.

10. The process of making micro-sized protein particles as claimed in claim 9, wherein said high shear condition is characterized by a Reynold's number in the range of 2000 to 200,000.

11. The process of making micro-sized protein particles as claimed in claim 1, wherein said spray-drying step is undertaken without the use of a binder to agglomerate said nano-sized protein particles.

12. The process of making micro-sized protein particles as claimed in claim 1, wherein said protein is biologically active to a target.

13. The process of making micro-sized protein particles as claimed in claim 12, wherein said spray-drying does not substantially degrade the biologically activity of said protein.

14. The process of making micro-sized protein particles as claimed in claim 12, further comprising a protein that is not biologically active to a target.

15. A micro-sized protein particle having a porous structure and comprised of a plurality of agglomerated nano-sized protein particles, said nano-sized protein particles having a narrow particle size distribution with a span value of less than 3, wherein the micro-sized protein particle is suitable for use as a formulation for pulmonary delivery.

16. The micro-sized protein particle as claimed in claim 15, wherein said micro-sized protein particle has a particle size in the range from 1 μm to 10 μm.

17. The micro-sized protein particle as claimed in claim 15, wherein said micro-sized protein particle has a substantially spherical shape.

18. The micro-sized protein particle as claimed in claim 15, wherein the porosity of said micro-sized protein particle is in the range of 10% to 80%.

19. The micro-sized protein particle as claimed in claim 15, wherein said micro-sized protein particle has a porous inner core.

20. The micro-sized protein particle as claimed in claim 15, wherein said micro-sized protein particle has a void in the inner core.

* * * * *